(12) United States Patent
Budow et al.

(10) Patent No.: US 8,981,070 B2
(45) Date of Patent: Mar. 17, 2015

(54) CONJUGATE BETWEEN A THIOPHILIC SOLID PHASE AND AN OLIGONUCLEOTIDE COMPRISING A THIOOXONUCLEOTIDE

(71) Applicant: Roche Diagnostics Operations, Inc., Indianapolis, IN (US)

(72) Inventors: Simone Budow, Tecklenburg (DE); Ping Ding, Muenster (DE); Dieter Heindl, Paehl (DE); Alfons Nichtl, Hohenpeissenberg (DE); Frank Seela, Osnabrueck (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/866,412

(22) Filed: Apr. 19, 2013

(65) Prior Publication Data

US 2013/0210009 A1    Aug. 15, 2013

Related U.S. Application Data

(63) Continuation of application No. PCT/EP2011/005321, filed on Oct. 21, 2011.

(30) Foreign Application Priority Data

Oct. 22, 2010    (EP) .................................. 10188515

(51) Int. Cl.
| | |
|---|---|
| *C07H 21/02* | (2006.01) |
| *C07H 21/00* | (2006.01) |
| *C12Q 1/68* | (2006.01) |

(52) U.S. Cl.
CPC ...................................... *C07H 21/02* (2013.01)
USPC .......... 536/23.1; 536/24.3; 536/25.3; 435/6.1

(58) Field of Classification Search
USPC .......................... 536/23.1, 24.3, 25.3; 435/6.1
See application file for complete search history.

(56) References Cited

U.S. PATENT DOCUMENTS

| | | | |
|---|---|---|---|
| 5,990,749 A | 11/1999 | Mohapatra et al. | |
| 6,274,323 B1 | 8/2001 | Bruchez et al. | |

(Continued)

FOREIGN PATENT DOCUMENTS

| | | |
|---|---|---|
| CN | 1959394 A | 5/2007 |
| WO | 2007/059816 A1 | 5/2007 |

OTHER PUBLICATIONS

International Search Report issued Dec. 20, 2011 in Application No. PCT/EP2011/005321, 5 pages.

(Continued)

*Primary Examiner* — Jezia Riley
(74) *Attorney, Agent, or Firm* — Roche Diagnostics Operations, Inc.

(57) ABSTRACT

An oligonucleotide-solid phase conjugate, wherein the solid phase is thiophilic and the oligonucleotide comprises at least one thiooxonucleobase according to Formula I,

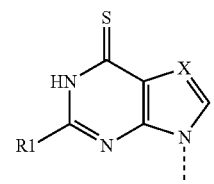

wherein X is CH or N, R1 is H or NH2, --- indicates a covalent bond, and said oligonucleotide is bound to said solid phase via the sulfur atom of said thiooxonucleotide. Also disclosed are methods for producing such conjugate as well as various uses for such oligonucleotide metal conjugate.

15 Claims, 14 Drawing Sheets

(56) References Cited

U.S. PATENT DOCUMENTS

| | | |
|---|---|---|
| 6,322,901 B1 | 11/2001 | Bawendi et al. |
| 2002/0076717 A1 | 6/2002 | Makino et al. |

OTHER PUBLICATIONS

Chan, Cangel Pui-yee, "Ingenious nanoprobes in bioassays," Bioanalysis, 2009, pp. 115-133, vol. 1, No. 1.
Christopherson, Michael S. and Broom, Arthur D., "Synthesis of oligonucleotides containing 2'-deoxy-6-thioguanosine at a predetermined site," Nucleic Acids Research, 1991, pp. 5719-5724, vol. 19, No. 20.
Csáki, Andrea et al., "Gold nanoparticles as novel label for DNA diagnostics," Expert Review of Molecular Diagnostics, 2002, pp. 187-193, vol. 2, No. 2.
Demers, Linette M., "A Fluorescence-Based Method for Determining the Surface Coverage and Hybridization Efficiency of Thiol-Capped Oligonucleotides Bound to Gold Thin Films and Nanoparticles," Analytical Chemistry, 2000, pp. 5535-5541, vol. 72, No. 22.
Elghanian, Robert et al., "Selective Colorimetric Detection of Polynucleotides Based on the Distance-Dependent Optical Properties of Gold Nanoparticles," Science, 1997, pp. 1078-1081, vol. 277.
Erler, Christiane and Mertig, Michael, "Incorporation of DNA networks into microelectrode structures," Journal of Vacuum Science & Technology B, Mar./Apr. 2009, pp. 939-943, vol. 27, No. 2.
Fox, Jack J. et al., "Thiation of Nucleosides. II. Synthesis of 5-Methyl-2'-deoxycytidine and Related Pyrimidine Nucleosides," American Journal of the Chemical Society, 1959, pp. 178-187, vol. 81.
Gothelf, Kurt V. and LaBean, Thomas H., "DNA-programmed assembly of nanostructures," Organic and Biomolecular Chemistry, 2005, pp. 4023-4037, vol. 3.
Hacia, Joseph G. et al., "Design of modified oligodeoxyribonucleotide probes to detect telomere repeat sequences in FISH assays," Nucleic Acids Research, 1999, pp. 4034-4039, vol. 27, No. 20.
Hurst, Sarah J. et al., "Maximizing DNA Loading on a Range of Gold Nanoparticle Sizes," Analytical Chemistry, Dec. 2006, pp. 8313-8318, vol. 78, No. 24.
Iwamoto, R. H. et al., "2'-Deoxythioguanosine and Related Nucleosides," Journal of Medicinal Chemistry, 1963, pp. 684-688, vol. 6.
Jin, Rongchao et al., "What Controls the Melting Properties of DNA-Linked Gold Nanoparticle Assemblies?," Journal of the American Chemical Society, 2003, pp. 1643-1654, vol. 125.
Kafka, J. et al., "A label-free DNA sensor based on impedance spectroscopy," Electrochimica Acta, 2008, pp. 7467-7474, vol. 53.
Mahtab, Rahina et al., "Protein-Sized Quantum Dot Luminescence Can Distinguish between "Straight", "Bent", and "Kinked" Oligonucleotides," Journal of the American Chemical Society, 1995, pp. 9099-9100, vol. 117.
Mahtab, Rahina et al., "Temperature- and Salt-Dependent Binding of Long DNA to Protein-Sized Quantum Dots: Thermodynamics of "Inorganic Protein"—DNA Interactions," Journal of the American Chemical Society, 2000, pp. 14-17, vol. 122.
Mirkin, Chad A. et al., "A DNA-based method for rationally assembling nanoparticles into macroscopic materials," Nature, Aug. 1996, pp. 607-609, vol. 382.
Mitchell, Gregory P. et al., "Programmed Assembly of DNA Functionalized Quantum Dots," Journal of the American Chemical Society, 1999, pp. 8122-8123, vol. 121.
Möller, Robert and Fritzsche, Wolfgang, "Chapter 10, Biosensors Based on Gold Nanoparticle Labeling," Annual Review of Nano Research (Guozhong Cao and C. Jeffrey Brinker, Editors), 2006, pp. 429-466, vol. 1, World Scientific, New Jersey.
Murphy, Catherine J., "Optical Sensing with Quantum Dots," Analytical Chemistry, Oct. 2002, pp. 520A-526A.
Nastasijevic, Branislav et al., "Sequence-specific binding of DNA and RNA to immobilized Nickel ions," Biochemical and Biophysical Research Communications, 2008, pp. 420-425, vol. 366.
Niemeyer, Christof M., "Self-assembled nanostructures based on DNA: towards the development of nanobiotechnology," Current Opinion in Chemical Biology, 2000, pp. 609-618, vol. 4.
Reynolds, Robert A. III, et al., "A gold nanoparticle/latex microsphere-based colorimetric oligonucleotide detection method," Pure Applied Chemistry, 2000, pp. 229-235, vol. 72, Nos. 1-2.
Seela, Frank and Budow, Simone, "pH-Dependent Assembly of DNA-Gold Nanoparticles Based on the i-Motif: A Switchable Device with the Potential of a Nanomachine," Helvetica Chimica Acta, 2006, pp. 1978-1985, vol. 89.
Seela, Frank et al., "Ion-Specific Aggregation of Gold-DNA Nanoparticles Using the dG Quartet Hairpin 5'-d (G4T4G4)," Chemistry & Biodiversity, 2005, pp. 84-91, vol. 2.
Seela, Frank et al., "Oligonucleotides forming an i-motif: the pH-dependent assembly of individual strands and branched structures containing 2'-deoxy-5-propynylcytidine," Organic & Biomolecular Chemistry, 2007, pp. 1858-1872, vol. 5.
Seela, Frank and Becher, Georg, "Pyrazolo[3,4-d]pyrimidine nucleic acids: adjustment of dA-dT to dG-dC base pair stability," Nucleic Acids Research, 2001, pp. 2069-2078, vol. 29, No. 10.
Seeman, Nadrian C., "DNA in a material world," Nature, Jan. 2003, pp. 427-431, vol. 421.
Storhoff, James J. et al., "One-Pot Colorimetric Differentiation of Polynucleotides with Single Base Imperfections Using Gold Nanoparticle Probes," Journal of the American Chemical Society, 1998, pp. 1959-1964, vol. 120.
Taton, T. Andrew et al., "Scanometric DNA Array Detection with Nanoparticle Probes," Science, Sep. 2000, pp. 1757-1760, vol. 289.
Thanh, Nguyen Thi Kim and Rosenzweig, Zeev, "Development of an Aggregation-Based Immunoassay for Anti-Protein A Using Gold Nanoparticles," Analytical Chemistry, Apr. 2002, pp. 1624-1638, vol. 74, No. 7.
Turkevich, John et al., "A Study of the Nucleation and Growth Processes in the Synthesis of Colloidal Gold," Discussions of the Faraday Society, 1951, pp. 55-75, vol. 11.
Vorbrüggen, Helmut and Strehlke, Peter, "Eine einfache Synthese von 2-Thiopyrimidin-nucleosiden," Chem. Ber., 1973, vol. 106 Abstract only.

| Compound / Name (Synonyme(s)) | Structure / Formula / Sequence | SEQ ID NO. |
|---|---|---|
| Compound 1 (1, thiooxonucleoside 1, nucleoside 1, thionucleoside 1) | 7-deaza-6-thio-2'-deoxyguanosine | |
| Compound 2 (2) | 7-(2-Deoxy-β-D-erythro-pentofuranosyl)-2-phenoxyacetamino-7H-pyrrolo[2,3-d]pyrimidin-4(3H)-thione | |
| Compound 3 (3) | 4-[(2-Cyanoethyl)thio]-7-(2-deoxy-β-D-erythro-pentofuranosyl)-2-phenoxyacetamino-7H-pyrrolo[2,3-d]pyrimidine | |
| Compound 4 (4) | 4-[(2-Cyanoethyl)thio]-7-[2-deoxy-5-O-(4,4'-dimethoxytrityl)-β-D-erythro-pentofuranosyl]-2-phenoxyacetamino-7H-pyrrolo[2,3-d]pyrimidine | |
| Compound 5 (5) | 4-[(2-Cyanoethyl)thio]-7-[2-deoxy-5-O-(4,4'-dimethoxytrityl)-β-D-erythro-pentofuranosyl]-2-phenoxyacetamino-7H-pyrrolo[2,3-d]pyrimidine 3'-[(2-cyanoethyl)-N,N-diisopropylphosphoramidite] | |
| Compound 26 (26, thiooxonucleoside 26, nucleoside 26, thionucleoside 26) | 4-thio-2'-deoxythymidine | |
| Compound 27 (27, thiooxonucleoside 27, nucleoside 27, thionucleoside 27) | 2-thio-2'-deoxythymidine | |
| Compound 28 (28, thiooxonucleoside 28, nucleoside 28, thionucleoside 28) | 6-thio-2'-deoxyguanosine | |
| Compound 38 (38) | Phosphoramidite (Chemical structure shown in Figure 10) | |

Fig. 11 (contd.)

| | | |
|---|---|---|
| Compound 39 (39) | Phosphoramidite (Chemical structure shown in Figure 10) | |
| Compound 40 (40) | Phosphoramidite (Chemical structure shown in Figure 10) | |
| oligonucleotide 6 (6) | 5'-d(AGT ATT GAC CTA AIT ATT GAC CTA) | 1 |
| oligonucleotide 7 (7) | 3'-d(ATC CAI TTA TGA) | 2 |
| oligonucleotide 8 (8) | 5'-d(I T$_{10}$ TAG GTC AAT ACT) | 3 |
| oligonucleotide 9 (9) | 5'-d(I T$_{10}$ AGT ATT GAC CTA) | 4 |
| oligonucleotide 10 (10) | 5'-d(TAG GTC AAT ACT) | 5 |
| oligonucleotide 11 (11) | 3'-d(ATC CAG TTA TGA) | 6 |
| oligonucleotide 12 (12) | 3'-d(ATC CAG TTA TIA) | 7 |
| oligonucleotide 13 (13) | 5'-d(TAI ITC AAT ACT) | 8 |
| oligonucleotide 14 (14) | 3'-d(ATC CAI TTA TIA) | 9 |
| oligonucleotide 15 (15) | 5'-d(II T$_{10}$ TAG GTC AAT ACT) | 10 |
| oligonucleotide 16 (16) | 5'-d(II T$_{10}$ AGT ATT GAC CTA) | 11 |
| oligonucleotide 17 (17) | 5'-d(III T$_{10}$ TAG GTC AAT ACT) | 12 |
| oligonucleotide 18 (18) | 5'-d(III T$_{10}$ AGT ATT GAC CTA) | 13 |
| oligonucleotide 19 (19) | 5'-d(TAG GTC AAT ACT TAG GTC AAT ACT) | 14 |
| oligonucleotide 20 (20) | 3'-d(ATC CAG TTA TGA ATC CAG TTA TGA) | 15 |
| oligonucleotide 21 (21) | 5'-d(TAI GTC AAT ACT TAG GTC AAT ACT) | 16 |
| oligonucleotide 22 (22) | 5'-d(AIT ATT GAC CTA AGT ATT GAC CTA) | 17 |
| oligonucleotide 23 (23) | 5'-d(TAG GTC AAT ACT TAI GTC AAT ACT) | 18 |
| oligonucleotide 24 (24) | 5'-d(Trityl-S-(CH$_2$)$_6$ T$_{10}$ TAG GTC AAT ACT) | 19 |

Fig. 11 (contd.)

| | | |
|---|---|---|
| oligonucleotide 25 (25) | 5'-d(Trityl-S-(CH₂)₆ T₁₀ AGT ATT GAC CTA) | 20 |
| oligonucleotide 32 (32) | 5'-d(26 T₁₀ TAG GTC AAT ACT) | 21 |
| oligonucleotide 33 (33) | 5'-d(26 T₁₀ AGT ATT GAC CTA) | 22 |
| oligonucleotide 34 (34) | 5'-d(27 T₁₀ TAG GTC AAT ACT) | 23 |
| oligonucleotide 35 (35) | 5'-d(27 T₁₀ AGT ATT GAC CTA) | 24 |
| oligonucleotide 36 (36) | 5'-d(28 T₁₀ TAG GTC AAT ACT) | 25 |
| oligonucleotide 37 (37) | 5'-d(28 T₁₀ AGT ATT GAC CTA) | 26 |
| Au6 (gold particle coated with oligonucleotide 6) | 5'-d(AGT ATT GAC CTA A⫯T ATT GAC CTA) (Au6) | 1 |
| Au8 (gold particle coated with oligonucleotide 8) | 5'-d(⫯ T₁₀ TAG GTC AAT ACT) (Au8) | 3 |
| Au9 (gold particle coated with oligonucleotide 9) | 5'-d(⫯ T₁₀ AGT ATT GAC CTA) (Au9) | 4 |
| Au15 (gold particle coated with oligonucleotide 15) | 5'-d(⫯⫯ T₁₀ TAG GTC AAT ACT) (Au15) | 10 |
| Au16 (gold particle coated with oligonucleotide 16) | 5'-d(⫯⫯ T₁₀ AGT ATT GAC CTA) (Au16) | 11 |
| Au17 (gold particle coated with oligonucleotide 17) | 5'-d(⫯⫯⫯ T₁₀ TAG GTC AAT ACT) (Au17) | 12 |
| Au18 (gold particle coated with oligonucleotide 18) | 5'-d(⫯⫯⫯ T₁₀ AGT ATT GAC CTA) (Au18) | 13 |
| Au21 (gold particle coated with oligonucleotide 21) | 5'-d(TA⫯ GTC AAT ACT TAG GTC AAT ACT) (Au21) | 16 |

Fig. 11 (contd.)

| Au22 (gold particle coated with oligonucleotide 22) | 5'-d(A T ATT GAC CTA AGT ATT GAC CTA) (Au22) | 17 |
|---|---|---|
| Au23 (gold particle coated with oligonucleotide 23) | 5'-d(TAG GTC AAT ACT TA T GTC AAT ACT) (Au23) | 18 |
| Au24 (gold particle coated with oligonucleotide 24) | 5'-d(S-(CH$_2$)$_6$-T$_{10}$ TAG GTC AAT ACT) (Au24) | 19 |
| Au25 (gold particle coated with oligonucleotide 25) | 5'-d(S-(CH$_2$)$_6$-T$_{10}$ AGT ATT GAC CTA) (Au25) | 20 |
| Spacer T$_{10}$ (T$_{10}$) | 5'-d(TTT TTT TTT T) | 27 |

CONJUGATE BETWEEN A THIOPHILIC SOLID PHASE AND AN OLIGONUCLEOTIDE COMPRISING A THIOOXONUCLEOTIDE

CROSS-REFERENCE TO RELATED APPLICATIONS

This application is a continuation of International Application No. PCT/EP2011/005321, filed Oct. 21, 2011, which claims the benefit of European Patent Application No. 10188515.0, filed Oct. 22, 2010, the disclosures of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Apr. 3, 2013, is named 27094US_SEQ_LIS-TING.txt, and is eight thousand and sixty-three bytes in size.

BACKGROUND OF THE DISCLOSURE

Conjugation of biomolecules to solid surfaces is utilized in some forms of diagnostic applications, for example in immuno assays or nucleic acid arrays, both requiring the binding of a biomolecule to a solid phase. Different solid phase materials are available for various applications, including polystyrene or latex surfaces or particles, and also metal coated surfaces, metal particles and quantum dots, for example.

Among known metal nanoparticles, quantum dots and gold nanoparticles (AuNPs) gained particular attention due to their chemical inertness and the ease of surface modification (Mitchell, G. P. et al., J. Am. Chem. Soc. 121 (1999) 8122-8123; Mahtab, R. et al., J. Am. Chem. Soc. 117 (1995) 9099-9100; Mahtab, R. et al., J. Am. Chem. Soc. 122 (2000) 14-17; Reynolds III, R. A. et al., Pure Appl. Chem. 72 (2000) 229-235; Thanh, N. T. et al., Anal. Chem. 74 (2002) 1624-1628; Csáki, A. et al., Exp. Rev. Mol. Diagn. 2 (2002) 187-193; Thaxton, C. S., and Mirkin, C. A. in: Nanobiotechnology, Niemeyer, C. M., and Mirkin, C. A. (eds.), Wiley-VCH, Weinheim (2004) pp. 288-307).

For example, DNA may be coupled to gold nanoparticles. A DNA gold nanoparticle conjugate system (DNA-AuNPs) may be utilized for different applications e.g. for biosensors used for in vitro diagnostics, for in vivo imaging, as drug carrier, and for building up defined nanostructures, for example.

BRIEF SUMMARY OF THE DISCLOSURE

The present disclosure provides an oligonucleotide-solid phase conjugate, wherein the solid phase is thiophilic and the oligonucleotide comprises at least one thiooxonucleobase according to Formula I,

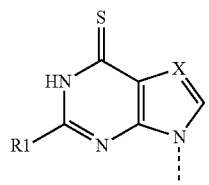

wherein X is CH or N, wherein R1 is H or NH2, wherein --- indicates a covalent bond, and wherein said oligonucleotide is bound to said solid phase via the sulphur atom of said thiooxonucleotide. The present disclosure also provides methods for producing such conjugate as well as various uses for such oligonucleotide metal conjugate.

According to some embodiments of the instant disclosure, a method of producing an oligonucleotide-solid phase conjugate is provided. According to some embodiments, the method comprises the steps of (a) providing a thiophilic solid phase selected from the group consisting of a thiophilic metal, an inorganic oxide, sulfide, selenide or telluride comprising a thiophilic metal, e.g. as in Cd based quantum dots and (b) binding an oligonucleotide containing at least one thiooxonucleobase according to Formula I, as given and defined above, to said thiophilic solid phase.

Other embodiments of the instant disclosure include various uses like the use of an oligonucleotide-solid phase conjugate according to the present disclosure in a detection method based on nucleic acid hybridization or the use of an oligonucleotide nanoparticle conjugate as a label are also disclosed and described.

BRIEF DESCRIPTION OF THE DRAWINGS

The features of this disclosure, and the manner of attaining them, will become more apparent and the disclosure itself will be better understood by reference to the following description of embodiments of the disclosure taken in conjunction with the accompanying drawing.

FIG. 11 presents and summarizes chemical compounds and the sequences used, as well as the various gold particles coated with a sequence of interest.

Figure 1:
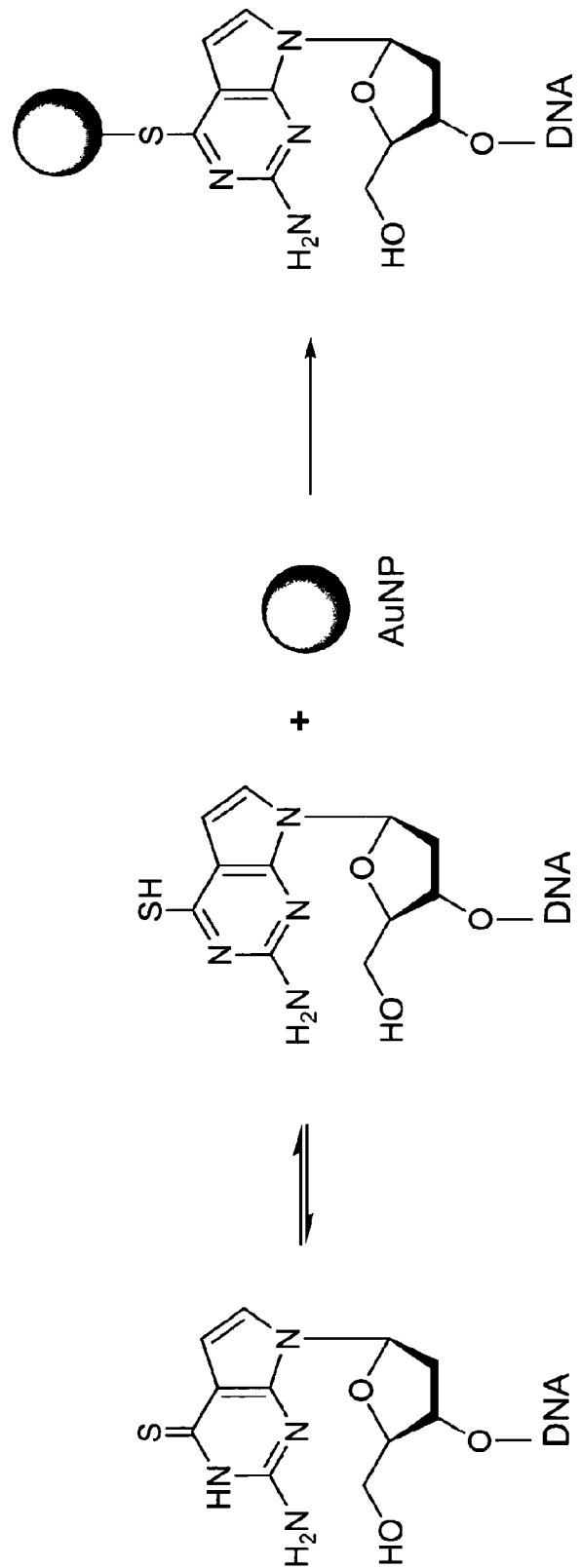
FIG. 1 is a schematic of a reaction route for the formation of an oligonucleotide gold conjugate (AuNP) between an oligonucleotide comprising a selected example of a thiooxonucleoside with a nucleobase according to Formula I as an anchor molecule is given schematically.

Corresponding reference characters indicate corresponding parts throughout the several views. Although the drawings represent embodiments of the present disclosure, the drawings are not necessarily to scale and certain features may be exaggerated in order to better illustrate and explain the present disclosure. The exemplifications set out herein illustrate an exemplary embodiment of the disclosure, in one form, and such exemplifications are not to be construed as limiting the scope of the disclosure in any manner.

DETAILED DESCRIPTION OF THE DISCLOSURE

The embodiments disclosed herein are not intended to be exhaustive or limit the disclosure to the precise form disclosed in the following detailed description. Rather, the embodiments are chosen and described so that others skilled in the art may utilize their teachings.

As discussed herein, it is possible to couple DNA to gold nanoparticles. DNA gold nanoparticle conjugate systems ("DNA-AuNPs") provide for combining favourable properties of gold colloids with those of DNA. The DNA molecule has (i) unique molecular recognition properties, (ii) it is easily accessed by automated DNA synthesis or enzymatic polymerization, (iii) single-stranded oligonucleotides have the capability to form multi-stranded aggregates allowing the construction of nanoscaled devices (See, for example, Seeman, N. C., Nature 421 (2003) 427-431; Niemeyer, C. M., Curr. Opin. Chem. Biol. 4 (2000) 609-618; Gothelf, K. V. et al., Org. Biom. Chem. 3 (2005) 4023-4037; Seela, F. and Budow, S., Helv. Chim. Acta 89 (2006) 1978-1985; Seela, F. et al., Org. Biomol. Chem. 5 (2007) 1858-1872; Seela, F. et al., Chem. Biodiv. 2 (2005) 84-91). Furthermore, as discussed herein, gold nano particles or gold surfaces which are functionalized with oligonucleotides may act as core elements for different applications such as for biosensors used for in vitro diagnostics, for in vivo imaging, as drug carrier, and for building up defined nanostructures (see, for example, Letsinger, R. L. et al., Chemistry of Oligonucleotide—Gold Nanoparticle Conjugates, In: Phosphorus, Sulfur and Silicon and the Related Elements, Vol. 144-146 (1999) pp. 359-362; Ingenious nanoprobes in bioassays, Chan, Cangel Pui-yee, Bioanalysis 1 (2009) 115-133; and Biosensors based on gold nanoparticle labeling, Moeller, R., Annual Review of Nano Research 1 (2006) 429-466).

Conventionally, attachment of oligonucleotides onto gold nanoparticle (AuNP) surfaces utilizes oligonucleotides modified at their 5'- or 3'-termini by a thiol-group (see, Mirkin, C. A. et al., Nature 382 (1996) 607). Single-stranded oligonucleotides are functionalized at their 5'- or 3'-end, respectively with acyclic linkers carrying thiol groups. The thiol function is then used for the covalent immobilization to the AuNPs. However, such modification, after oligonucleotide synthesis, requires an additional coupling/handling step.

Certain other methods for conjugation of oligonucleotides onto gold nanoparticle (AuNP) surfaces are based on the use of thiol modified oligonucleotides. In these methods thiol groups are introduced during oligonucleotide synthesis by using "thiol modifier" phosphoramidites which are commercially available. The thiol group is either protected with a trityl group which needs special deprotection conditions using silver nitrate or is protected as disulfide which is cleaved by reduction with DTT. In both cases standard deprotection conditions are not suitable and an excess of these special deprotection reagents has to be removed thoroughly before attaching the oligonucleotide to the gold surface.

In some embodiments, instead of chemical synthesis of an oligonucleotide an enzymatic synthesis is also possible. None of the thiol modifier phosphoroamidites may be compatible with enzymatic incorporation into an oligonucleotide. For an enzymatic incorporation of gold reactive groups the compound 4-thio-thymidine triphosphate (4-thioTTP) was used (Incorporation of DNA networks into microelectrode structures; Erler, C. and Mertig, M., Journal of Vacuum Science & Technology, B: Microelectronics and Nanometer Structures—Processing, Measurement, and Phenomena 27 (2009) 939-943). The corresponding 4 Thio T Phosphoramidite is commercially available and can be used in the chemical synthesis of a desired thio-dT containing oligonucleotide. However S-alkyl 4 ThioT is very reactive towards nucleophils. Therefore oligonucleotides synthesized with 4 thio T have to be cleaved with NaSH in presence of ammonia. As mentioned before any remaining deprotection reagent has to be thoroughly removed. However, as will be shown in the Examples section, an oligonucleotide having 4-thio thymidine (4-thioT) incorporated therein is not very stable against hydrolysis under standard deprotection condition and in general may be subject to nucleophilic attack. This in turn would result in instability of a conjugate based on incorporation of said thionucleotide.

According to embodiments of the present disclosure, a cost-effective and simple procedure for synthesis of a thionucleotide comprising oligonucleotide and/or for attaching such oligonucleotide to a thiophilic metal, like gold or a quantum dot is provided. According to embodiments of the instant disclosure, the group which allows attachment of the oligonucleotide to a surface can be introduced into the oligonucleotide directly during chemical synthesis of an oligonucleotide without any need to depart from established standard oligonucleotide synthesis protocols.

Furthermore, as disclosed herein, it is surprisingly found that an oligonucleotide comprising one or more thiol groups can be easily synthesized by using, incorporating a thiooxonucleobase according to Formula I into such oligonucleotide.

The present disclosure employs some conventional techniques of molecular biology (including recombinant techniques), microbiology, cell biology, biochemistry, and immunology, which are within the skill of the art and are explained in the literature, such as, "Molecular Cloning: A Laboratory Manual", second edition (Sambrook et al., 1989); "Oligonucleotide Synthesis" (M. J. Gait, ed., 1984); "Animal Cell Culture" (R. 1. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., eds., 1994).

Technical and scientific terms used herein have the same meaning as commonly understood by one of ordinary skill in the art to which this disclosure belongs. Singleton et al., Dictionary of Microbiology and Molecular Biology $2^{nd}$ ed., J. Wiley & Sons (New York, N.Y., 1994); March, Advanced Organic Chemistry Reactions, Mechanisms and Structure, 4th ed., John Wiley & Sons (New York, N.Y., 1992); Lewin, B., Genes V, published by Oxford University Press (1994), ISBN 0-19-854287 9); Kendrew, J. et al. (eds.), The Encyclopedia of Molecular Biology, published by Blackwell Science Ltd. (1994), ISBN 0-632-02182-9); and Meyers, R. A. (ed.), Molecular Biology and Biotechnology: a Comprehensive Desk Reference, published by VCH Publishers, Inc. (1995), ISBN 1-56081-569 8), Mueller, S. (ed.) Nucleic Acids from A to Z, A Concise Encyclopedia, Wiley VCH 2008, ISBN-10: 3-527-31211-0) provide one skilled in the art with a general guide to many of the terms used in the present application.

As used herein, each of the following terms has the meaning associated with it in this section.

The articles "a" and "an" are used herein to refer to one or to more than one (i.e. to at least one) of the grammatical object of the article. By way of example, "an antibody" means one antibody or more than one antibody. The term "at least" is used to indicate that optionally one or more further objects may be present. By way of example, an array comprising at least two discrete areas may optionally comprise two or more discrete test areas.

The expression "one or more" denotes 1 to 50, and in some embodiments 1 to 20 or even 2, 3, 4, 5, 6, 7, 8, 9, 10, 12, or 15.

In some embodiments, the thiophilic metal may be an alloy, a semiconductor or a mixed metal semiconductor, comprising a thiophilic metal or it may essentially consist of a thiophilic metal, i.e. it may be a pure metal.

In case the thiophilic metal is a noble metal selected from the group consisting of copper, gold and silver, the thiophilic metal solid phase may consist of such metal. In case a thiophilic semiconductive material is used as a solid phase, the thiophilic metal may be comprised in such material but needs not to be present in its pure metallic form. In such semiconductor material the thiophilic metal may be present to at least 35% w/w. Also in some embodiments, such semiconductor material comprises at least 40%, 45% or 50%, of a thiophilic semiconductor metal.

In certain embodiments, particles (e.g. gold particles or quantum dots) may be utilized, while for other embodiments a layer of a thiophilic metal or a thiophilic semiconductive material coated onto a solid support material may be utilized. The term "solid phase" as used in the present disclosure is intended to cover both these alternatives, a) a solid phase made of a thiophilic metal and b) a solid phase wherein the thiophilic metal is present on the surface of a solid support material.

A solid support material to be coated with a thiophilic metal for forming a solid phase is not subject to any special restrictions and can be chosen for example from among metal (e.g. aluminum) surfaces, metal surfaces vapor-deposited with $SiO_2$, metal/semimetal oxide (e.g. $Al_2O_3$ or $SiO_2$) surfaces, glass surfaces, polymer surfaces, e.g. in film form, Nylon membranes or nitrocellulose membranes. However, it is clear to the person skilled in the art that basically "semisolid" or gel-like solid phase supports are also suitable.

The use of glass as a solid phase support represents an exemplary embodiment. Glass does not have a porous surface and allows for uniform coating with thiophilic metal or a semiconductive layer of a thiophilic inorganic oxide or sulfide. Glass also is mechanically robust, temperature-resistant and insensitive to rigorous washing conditions, and has a low intrinsic fluorescence. All types and kinds of glass are suitable, e.g. quartz glass.

The polymer solid phase support can consist, for example, of polypropylene, polymethylmethacrylate (PMMA) (acrylic glass or Plexiglass) or cycloolefine copolymers (COCs). For example a suitable COC is available from Ticona under the trade name "Topaz".

The term "conjugate" as used herein relates to the fact that an oligonucleotide comprising a thiooxo nucleotide is bound to a thiophilic metal comprised in the solid phase via a sulphur group comprised in said oligonucleotide. The exact chemical nature of the bond between a thiophilic metal and a thiol is still under investigation. An exemplary and illustrative embodiment of thiol-gold bonding is described and given below.

The gold-sulfur bond is a unique bond between gold and sulfur atoms in a sulfur compound, usually an organosulfur compound. Water-stable gold salts between gold and sulfur frequently feature gold in its +1 oxidation state (aurous gold), formed with soft ligands such as thioethers and thiolates. However, organosulfur compounds, even neutral thioethers and thiols, can also bind rather strongly to elemental gold surfaces, such as those found on colloidal gold nanoparticles, as well as the surfaces on bulk gold.

The electronics of the thiol-Au(0) surface bond is not exactly clear, but it tends to be approaching covalent because of gold's high electronegativity (2.4 on the Pauling scale and is rather strong (126-146 kJ/mol), which is rare for most surface bonds between neutral ligands and neutral zero-valent noble metals.

Numerous hypotheses have been proposed for the nature of this bond that has puzzled chemists for centuries, but it has been difficult to carry out experimental work that would rule out one hypothesis in favour of another. The bond probably features dative interactions and may feature backbonding. The bond energy for gold-sulfur interactions decreases as the surface becomes saturated with sulfur-containing compounds, such as in a self-assembled monolayer.

It is not fully understood what happens to the sulfhydryl hydrogen on a thiol when it binds to a gold surface. Competing hypotheses suggest it may leave as a proton, hydride or hydryl (H-dot) radical, perhaps stabilized by the gold or ultimately in the form of hydrogen. One group using proton NMR work suggests the hydrogen often may not leave at all. When excess thiol is used however (i.e. covering more than 50% of the gold surface), loss of hydrogen is "rapid and irreversible."

The term "thiophilic metal" is based on the HSAB-concept and describes the fact that soft sulfide is bound to a corresponding soft metal. The HSAB-concept is an acronym for hard and soft (Lewis) acids and bases. According to the HSAB concept soft metal ions prefer soft sulfide as a counter ion and are therefore also named thiophilic in contrast to hard oxophilic metal ions.

As illustrated already above for the thiophilic noble metal gold, the exact nature of the bond between the sulphur atom of a thiooxo group, e.g. as comprised in an oligonucleotide is not known. But this is not crucial as long as an appropriate thiophilic metal can be selected and the desired binding is achieved.

Thiophilic metals or metal ions according to the present disclosure include the group consisting of group 11: (Cu, Ag, Au); group 12 (Cd, Hg); group 13 (Ga, In, Tl) and group 14 (Sn, Pb) metals.

In an embodiment according to the present disclosure the thiophilic metal is selected from the group consisting of a thiophilic noble metal and a thiophilic semiconductive material.

In one embodiment the thiophilic metal is a noble metal selected from the group consisting copper, silver and gold. In one embodiment the thiophilic metal will be chosen from silver or gold. In one embodiment gold is used as thiophilic solid phase material. In one embodiment silver is used as thiophilic solid phase material.

As the skilled artisan appreciates a thiophilic semiconductor material may comprise one or more metal(s) selected from the group consisting of cadmium, gallium and indium this metal being present as an oxide, a sulphide or a selenide. In an exemplary embodiment the thiophilic semiconductor material is based on cadmium or gallium. In another exemplary embodiment the semiconductor material is based on cadmium.

In one embodiment the thiophilic semiconductor material is present in form of a nanocrystal or quantum dot. The term "quantum dot" is intended to be broadly read to encompass such structures generally. Quantum dots are described in the patent and technical literature, see for example U.S. Pat. Nos. 6,322,901, 5,990,749, and 6,274,323, and Murphy, C. J., Analytical Chemistry 74 (2002) 520A-526A, the disclosure of which are herewith incorporated by reference in their entirety. A quantum dot is a semiconductor particle that has all three dimensions confined to the 1- to 10-nm-length scale. Inorganic semiconductors include the Group 14 (old Group IV) elements silicon and germanium; compounds such as GaN, GaP, GaAs, InP, and InAs (collectively the III-V materials); and ZnO, ZnS, ZnSe, CdS, CdSe, and CdTe (II-VI materials).

Quantum dots are e.g. commercially available from Invitrogen Corp., Evident Technologies, and others.

One of the important elements on which the present disclosure resides is an oligonucleotide comprising at least one thiooxonucleobase according to Formula I,

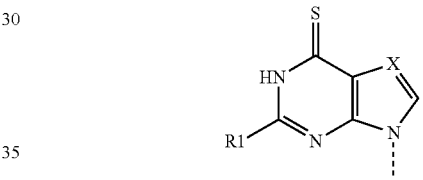

wherein X is CH or N, wherein R1 is H or NH2 and wherein --- indicates a covalent bond.

Via the N9 covalent bond the thiooxonucleobase according to Formula I is bound into the oligonucleotide part of the oligonucleotide-solid phase conjugate according to the present disclosure. The C atom of the oligonucleotide backbone to which the N9 atom is connected to is the same as the C— atom to which a naturally occurring purine nucleobase, i.e. an adenosine or a guanosine, is usually connected to the oligonucleotide backbone. In other words nucleobases according to Formula I are replacing a natural purine nucleobase, whereas the nature and positioning of the linkage to the backbone remains the same as with a naturally occurring purine nucleobase.

The thiooxonucleotide based on the nucleobase of Formula I can be present at the 5' and/or the 3'-end of an oligonucleotide or it can be part of a sequence of interest. In the latter case, with other words, the thiooxonucleobase according to Formula I replaces one or more of the nucleobases otherwise present in an oligonucleotide sequence of interest.

The oligonucleotide comprised in a conjugate according to embodiments of the present disclosure includes a nucleobase according to Formula I comprised therein. This nucleobase is e.g. mediating the binding of such oligonucleotide to a thiophilic solid phase.

The kind of backbone to which the nucleobase is connected via the N9 atom by covalent bond can vary in many different ways. The oligonucleotide being part of a complex according to the present disclosure or used to coat a thiophilic metal in a method according to this disclosure may have a standard phosphoribose backbone, wherein the ribosyl sugar moiety is selected from the group consisting of 2'deoxy D-ribose, 2'3'-dideoxy D-ribose and D-ribose, or may have any appropriate non-standard backbone.

Oligonucleotides with a non-standard backbone may comprise a ribosyl analog selected from the group consisting of: 2'deoxy L-ribose, 2'O-methyl, 2'fluoro RNA or have a backbone selected from locked nucleic acids (LNA), hexitol nucleic acids (HNA), cyclohexenyl nucleic acid (CeNA), altritol nucleic acid (ANA), peptide nucleic acids (PNA), Glycol nucleic acids (GNA), threose nucleic acid (TNA) and morpholino oligonucleotides.

The term nucleoside (or thiooxonucleoside) as used in the present disclosure, is not limited to nucleosides with standard 2'deoxy D-ribose, 2'3'-dideoxy D-ribose and D-ribose as sugar unit but also includes any combination of a standard nucleobase (or the heterocyclic nucleobase according Formula I) with a ribosyl analog or a structural analog of a sugar unit as e.g. used in locked nucleic acids (LNA), hexitol nucleic acids (HNA), cyclohexenyl nucleic acid (CeNA), altritol nucleic acid (ANA), peptide nucleic acids (PNA), Glycol nucleic acids (GNA), threose nucleic acid (TNA) and morpholino oligonucleotides.

Furthermore, in some embodiments, if a nucleobase according Formula I is present in an oligonucleotide, then the oligonucleotide can be attached to thiophilic solid supports. This is true for nucleotides based on standard ribosyl sugar backbone moieties as well as for oligonucleotides based on non-standard backbone structures as described above, as well as for chimeras of oligonucleotides with different types of backbone within one oligonucleotide.

For incorporation of nucleotides with a nucleobase of Formula I into an oligonucleotide via solid phase synthesis the corresponding monomers (e.g. phosphoroamidites) can be synthesized by using procedures which known for the synthesis of standard DNA and RNA oligonucleotides or for the synthesis of monomers for backbone modified oligonucleotides.

In some embodiments, the beta cyano ethyl phosphoroamidites of nucleosides with a protected nucleobase according to Formula I with 2'deoxyribose as the sugar unit are used, for example for economic reasons and ease of synthesis. Also, in some embodiments, 3'phosphoroamidites for 3'->5' synthesis may be used.

For incorporation of nucleotides with a nucleobase of Formula I into an oligonucleotide via enzymatic methods using a polymerase or a terminal transferase the corresponding triphosphate has to be synthesized. Incorporation of modified nucleoside triphosphates is known, but is limited to selected structures (e.g. HNA and ANA can be assembled by polymerases in addition to the normal ribosyl sugar triphosphates). Preferred for enzymatic synthesis are the triphosphates with D-ribose 2'deoxy D-ribose and 2'3' dideoxyDribose as the sugar unit of the nucleoside triphosphate.

The expression "nucleotide based on a nucleoside" is used to make clear that the nucleoside of Formula I has to be activated, e.g. phosphorylated for incorporation into an oligonucleotide and once incorporated into an oligonucleotide represents a nucleotide. Such nucleotide is then said to be derived from or based on the nucleoside with a nucleobase of Formula I.

The term "oligonucleotide," as used herein, generally refers to short, generally single stranded, polynucleotides that comprise at least 8 nucleotides and at most about 1000 nucleotides. In an exemplary embodiment an oligonucleotide will have a length of at least 9, 10, 11, 12, 15, 18, 21, 24, 27 or 30 nucleotides. In another exemplary embodiment an oligonucleotide will have a length of no more than 1000, 500, 300, 200, 150, 100, 90, 80, 70, 60, 50, 45, 40, 35 or 30 nucleotides. The description given below for polynucleotides is equally and fully applicable to oligonucleotides.

The term oligonucleotide is very broad and refers to polymers of nucleotides of any length, and includes DNA and RNA and analogs and modification thereof.

If thionucleotides according to the disclosure are to be incorporated during solid phase oligonucleotide only monomeric building blocks and modifying conditions (e.g. using a different oxidizer as described in WO 2007/059816) are used which can be combined within one synthesis chemistry with the monomeric thionucleoside building blocks.

The term oligonucleotide includes oligonucleotides with natural bases which are substituted at the nucleobase, e.g. with methyl, propargyl, or halogen, or where a pendant moiety or a functional group is attached to the nucleobase. If required, a modification to the nucleotide structure may be imparted before or after assembly of the polymer. An oligonucleotide may be further modified after polymerization, such as by conjugation with a labeling component. The sequence of nucleotides may be interrupted by non-nucleotide components. Non nucleosidic components are spacer and linkers which are non-functionalized or are functionalized with a reactive group like —NH2, —N3 —OH, —COOH, —C≡C, ONH2 or a linked to a pendant moiety. Pendant moieties are proteins (e.g., nucleases, toxins, antibodies, peptides, poly-L-lysine, etc.), intercalators (e.g., acridine, psoralen, etc.), minor groove binders (e.g. distamycin), chelators (e.g., metals, including radioactive metals and boron), fluorescent or non-fluorescent dyes (e.g., coumarines, fluoresceines, rhodamines, oxazines, 4,4-difluoro-4-bora-3a, 4a-diaza-s-indacene dyes (Bodipy), azodyes, polyazodyes, cyanines, merocyanines, stilbenes, perylens, pyrenes, phthalocyanines) and haptens (like biotin, digoxigenin).

The term oligonucleotide includes oligonucleotides with standard bases and/or with base analogs (analogs that show the same hydrogen bonding pattern as the natural bases) like C nucleosides (formycin, pseudo uridine), 7 deaza purines, 7 deaza 8 aza purines, and 6 aza pyrimidines. Such base analogs can also be further substituted e.g. alike 7 Br 7 deaza dG.

Nonstandard bases, e.g. universal bases like nitroindol, nitro pyroll and non-hydrogen bonding base surrogates (e.g. difluorphenyl) and non-natural bases which are capable of forming a third base pair (like iso dG or iso dC) are also modifications which are compatible with the immobilization method according to the disclosure.

The term oligonucleotide includes oligonucleotides with backbone modifications e.g. oligonucleotides with substituted deoxyribose (e.g. 2'fluoro or methoxy), with sugar analogs like bicyclic sugars (known as LNA) or 6 ring sugars analogs e.g. hexitol (known as HNA) as well as backbones with modified internucleosidic linkages like methylphosphonate, phosphoroamidites and phosphoro thioate. Not all linkages in a polynucleotide need be identical.

The term oligonucleotide also includes branched oligonucleotides, wherein at least three oligonucleotides are linked to each other via a branching unit. Different monomers for synthesis of branched oligonucleotides (e.g. 1-[5-(4,4'-dimethoxytrityloxy)pentylamido]-3-[5-fluorenomethoxy-carbonyloxypentylamido]-propyl-2-[(2-cyanoethyl)-(N,N-diisopropyl)]-phosphoramidite) are commercially available.

In one embodiment further groups in the oligonucleotide are present as modifications which are also capable of reacting with thiophilic surfaces e.g. like phosphorthioate or a thiol group on a non nucleotidic spacer such modifications are located in close proximity to the thionucleosides according to the disclosure in order not to have different reactive sites which can react with thiophilic surfaces. If thionucleotides according to the disclosure are incorporated as a triphosphate during enzymatic synthesis using a polymerase, the number and kind of nucleotide modifications in the amplificate is limited by the acceptance of the polymerase for those modified nucleotide triphosphates. Well incorporated are 5 substituted (d)CTP and (d)UTP, 7 substituted 7deaza-(d)GTP and 7 deaza-(d)ATP wherein the substituents are non-bulky substituents (e.g. alike in 5 Br dUTP, 5 Ethinyl dUTP, 5-aminoallyl dUTP) or small pendant moieties (e.g. labels or haptens) or a functional group preferably with an —NH2, —N3, and —C≡C moiety connected via a 6 to 30 atom spacer to the 5 or 7 position.

If desired these functional groups can be modified further with e.g. by binding a protein thereto in order to obtain a modification with a large pendant moiety.

The term "array" or "microarray", as used herein refers to an ordered arrangement of hybridizable array elements, preferably polynucleotide probes (e.g., oligonucleotides), on a substrate. The substrate can be a solid substrate, such as a glass slide, or a semi-solid substrate, such as nitrocellulose membrane. The nucleotide sequences can be DNA, RNA, or any permutations thereof.

A "target sequence," "target nucleic acid" or "target protein," as used herein, is a polynucleotide or protein of interest, the detection of which is desired. Generally, a "template," as used herein, is a polynucleotide that contains the target nucleotide sequence. In some instances, the terms "target sequence," "template DNA," "template polynucleotide," "target nucleic acid," "target polynucleotide," and variations thereof, are used interchangeably.

"Amplification," as used herein, generally refers to the process of producing multiple copies of a desired sequence. "Multiple copies" mean at least 2 copies. A "copy" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable, but not complementary, to the template), and/or sequence errors that occur during amplification.

Expression/amount of a gene, protein or biomarker in a first sample is high or increased as compared to expression/amount in a second sample if the expression level/amount of the gene, gene product, e.g., protein or biomarker in the first sample is greater than the expression level/amount of the gene, gene product, e.g., protein or biomarker in the second sample. In one embodiment, the increase in expression level/amount of the gene, gene product, e.g., protein or biomarker in the first sample is at least about 1.5×, 1.75×, 2×, 3×, 4×, 5×, 6×, 7×, 8×, 9×, 10×, 25×, 50×, 75×, or 100× the expression level/amount of the respective gene, gene product, e.g., protein or biomarker in the second sample.

Expression/amount of a gene, protein or biomarker in a first sample is low or decreased as compared to expression/amount in a second sample if the expression level/amount of the gene, gene product, e.g., protein or biomarker in the first sample is less than the expression level/amount of the gene, gene product, e.g., protein or biomarker in the second sample. In one embodiment, the decrease in expression level/amount of the gene, gene product, e.g., protein or biomarker in the first sample is at least about 1.5×, 1.75×, 2×, 3×, 4×, 5×, 6×, 7×, 8×, 9×, 10×, 25×, 50×, 75×, or 100× lower than the expression level/amount of the respective gene, gene product, e.g., protein or biomarker in the second sample.

Expression levels/amount can be determined based on any suitable criterion known in the art, including but not limited to mRNA, cDNA, proteins, protein fragments and/or gene copy. Expression levels/amounts can be determined qualitatively and/or quantitatively. In one embodiment, the samples are normalized for both differences in the amount of RNA or protein assayed and variability in the quality of the RNA or protein samples used. Such normalization may be accomplished by measuring and incorporating the expression of certain normalizing genes, including well known housekeeping genes, such as GAPDH. Alternatively, normalization can be based on the mean or median signal of all of the assayed genes or a large subset thereof (global normalization approach). On a gene-by-gene basis, measured normalized amount of a patient tumor mRNA or protein is compared to the amount found in a reference set. Normalized expression levels for each mRNA or protein per tested tumor per patient can be expressed as a percentage of the expression level measured in the reference set. The expression level measured in a particular patient sample to be analyzed will fall at some percentile within this range, which can be determined by methods well known in the art.

"Detection" includes any means of detecting, including direct and indirect detection.

The term "sample," or "test sample" as used herein, refers to a composition that is obtained or derived from a subject of interest that contains a cellular and/or other molecular entity that is to be characterized and/or identified, for example based on physical, biochemical, chemical and/or physiological characteristics. In one embodiment, the definition encompasses blood and other liquid samples of biological origin and tissue samples such as a biopsy specimen or tissue cultures or cells derived therefrom. The source of the tissue sample may be solid tissue as from a fresh, frozen and/or preserved organ or tissue sample or biopsy or aspirate; blood or any blood constituents; bodily fluids; and cells from any time in gestation or development of the subject or plasma. Samples may be obtained from a subject prior to commencement of treatment (e.g., cancer treatment) or after commencement of treatment (e.g., cancer treatment). Samples may be obtained within 24 hours, 7, 10, 14, 28, 42, or 56 days after commencement of treatment (e.g., cancer treatment). The term "sample," or "test sample" includes biological samples that have been manipulated in any way after their procurement, such as by treatment with reagents, solubilization, or enrichment for certain components, such as proteins or polynucleotides, or embedding in a semi-solid or solid matrix for sectioning purposes. For the purposes herein a "section" of a tissue sample is meant a single part or piece of a tissue sample, e.g. a thin slice of tissue or cells cut from a tissue sample.

Samples include, but are not limited to, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof. In one embodiment, the sample is a clinical sample. In another embodiment, the sample is used in a diagnostic assay. In some embodiments, the sample is obtained from a primary or metastatic tumor. Tissue biopsy is often used to obtain a representative piece of tumor tissue. Alternatively, tumor cells can be obtained indirectly in the form of tissues or fluids that are known or thought to contain the tumor cells of interest. For instance, samples of lung cancer lesions may be obtained by resection, bronchoscopy, fine needle aspiration, bronchial brushings, or from sputum, pleural fluid or blood.

A "primer" is generally a short single stranded polynucleotide, generally with a free 3'-OH group, that binds to a target potentially present in a sample of interest by hybridizing with a target sequence, and thereafter promotes polymerization of a polynucleotide complementary to the target. The exact sequences of the outer and inner primers or probes are chosen by the person skilled in the art in accordance with the actual analytical problem. For example it can involve sequences that hybridize to DNA sequences that are specific to the microorganisms that are to be detected or differentiated. For example organism-specific sequences can be ascertained by sequence data base comparisons and if necessary "Alignment". Basically there is no limitation to DNA or nucleic acids in general as probes. Because of their known advantages, it is also possible to use DNA-PNA (peptide-nucleic acid) hybrids or chimeras. Modified nucleic acids (e.g. dI, dI-biotin, dU, dU-biotin) can also be used.

By "correlate" or "correlating" is meant comparing, in any way, the performance and/or results of a first analysis or protocol with the performance and/or results of a second analysis or protocol. For example, one may use the results of a first analysis or protocol in carrying out a second protocols and/or one may use the results of a first analysis or protocol to determine whether a second analysis or protocol should be performed. With respect to the embodiment of gene expression analysis or protocol, one may use the results of the gene expression analysis or protocol to determine whether a specific therapeutic regimen should be performed.

The word "label" when used herein refers to a conjugate according to the present disclosure when fused directly or indirectly to a reagent such as a nucleic acid probe or an antibody, thereby facilitating detection of the reagent to which it is conjugated or fused. When, e.g. an oligonucleotide-gold conjugate according to the present disclosure is fused to an antibody, such antibody can be detected via the label, i.e. the gold comprised in the oligonucleotide-gold conjugate.

The conjugate according to the present disclosure and its use:

In an embodiment the present disclosure relates to an oligonucleotide-solid phase conjugate, wherein the solid phase comprises a thiophilic metal, wherein the oligonucleotide comprises at least one thiooxonucleobase according to Formula I,

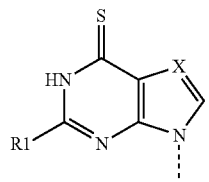

wherein X is CH or N, wherein R1 is H or NH2, wherein --- indicates a covalent bond, and wherein said oligonucleotide is bound to said solid phase via the sulphur atom of said thiooxonucleotide.

It has been found that the use of a thiooxonucleotide based on a thiooxonucleobase according to Formula I in the synthesis of an oligonucleotide is compatible with routine synthesis procedures. The thiooxonucleotide based on a nucleoside of Formula I can e.g. use in the chemical synthesis of an oligonucleotide and protection groups can be cleaved of according to standard protocols. In addition oligonucleotides comprising one or more nucleotide(s) according to Formula I can be firmly attached to a thiophilic solid phase.

An oligonucleotide wherein the thiooxonucleotide is a 6-deaza-thiooxonucleotide has the additional advantage that it is even more stable against any nucleophilic attack as compared to the 6-aza nucleotide. Therefore, in an exemplary embodiment X in Formula I is CH.

Thiophilic metals or metal ions according to the present disclosure may be selected from the group consisting of group 11: (Cu, Ag, Au); group 12 (Cd, Hg); group 13 (Ga, In, Tl) and group 14 (Sn, Pb) metals.

In an embodiment according to the present disclosure the thiophilic metal is selected from the group consisting of a thiophilic noble metal and a thiophilic semiconductive material. In one embodiment the oligonucleotide-solid phase conjugate comprises an oligonucleotide containing one or more thiooxonucleobase(s) of Formula I and a thiophilic solid phase selected from the group consisting of a thiophilic noble metal or a semiconductor material comprising a thiophilic metal.

In one embodiment the thiophilic metal comprised in the oligonucleotide-solid phase conjugate of the present disclosure is a noble metal selected from the group consisting of copper, silver and gold. In one embodiment the thiophilic metal is chosen from silver or gold. In one embodiment gold is used as thiophilic solid phase material. In one embodiment silver is used as thiophilic solid phase material.

As the skilled artisan appreciates a thiophilic semiconductor material may comprise one or more metal(s) selected from the group consisting of cadmium, gallium and indium this metal being present as an oxide, a sulphide, a telluride or a selenide. In an exemplary embodiment the thiophilic semiconductor material comprised in the oligonucleotide-solid phase conjugate of the present disclosure is based on cadmium or gallium.

In one embodiment the thiophilic semiconductor material comprised in the oligonucleotide-solid phase conjugate of the present disclosure is present in form of a nano crystal or quantum dot.

Since the nucleotide based on a nucleobase of Formula I can be easily incorporated into an oligonucleotide during synthesis, it is now also possible to insert such nucleotide at any desired position and in case two or more nucleotides based on a nucleobase of Formula I are to be incorporated this can be done at any desired distance from one such nucleotide to a neighboring one. In an embodiment the oligonucleotide-solid phase conjugate according to the present disclosure is formed between a thiophilic solid and an oligonucleotide comprising at least two nucleobases according to Formula I. Also in some embodiments, these two nucleotides with nucleobases according to Formula I may be separated by at least one other nucleotide and present at predefined positions in said oligonucleotide.

In an embodiment the oligonucleotide-solid phase conjugate according to the present disclosure is formed between a thiophilic solid and an oligonucleotide comprising at least one nucleobase according to Formula I wherein said oligonucleotide is at least 8 nucleotides in length.

In an embodiment the oligonucleotide-solid phase conjugate according to the present disclosure is formed between a thiophilic solid phase and an oligonucleotide comprising at least one nucleotide with a nucleobase according to Formula I wherein said oligonucleotide is at most 1000 nucleotides in length.

In some embodiments an oligonucleotide comprised in a conjugate according to the present disclosure has a length of at least 9, 10, 11, 12, 15, 18, 21, 24, 27 or 30 nucleotides, respectively. In some embodiments an oligonucleotide comprised in a conjugate according to the present disclosure has a length of no more than 1000, 500, 300, 200, 150, 100, 90, 80, 70, 60, 50, 45, 40, 35 or 30 nucleotides, respectively.

In an embodiment the present disclosure relates to a method of producing an oligonucleotide-solid phase conjugate, the method comprising the steps of (a) providing a solid phase comprising a thiophilic metal and (b) binding an oligonucleotide containing at least one thiooxonucleotide comprising a nucleobase according to Formula I,

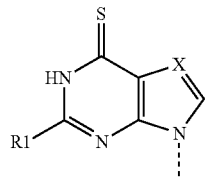

wherein X is CH or N, wherein R1 is H or NH2 and wherein -- indicates a covalent bond; to said thiophilic solid phase.

In one embodiment the method of producing an oligonucleotide-solid phase conjugate according to the present disclosure is practiced with an oligonucleotide comprising a nucleotide based on a nucleoside of Formula I, wherein X in Formula I is CH.

This method of producing an oligonucleotide-solid phase conjugate as disclosed herein is schematically depicted in FIG. 1.

Thiophilic metals or metal ions according to the present disclosure are preferably selected from the group consisting of group 11 (Cu, Ag, Au); group 12 (Cd, Hg); group 13 (Ga, In, Tl) and group 14 (Sn, Pb) metals.

In an embodiment the method as disclosed in the present disclosure is practiced with a thiophilic metal selected from the group consisting of a thiophilic noble metal and a thiophilic semiconductive material.

In an embodiment the method as disclosed in the present disclosure is practiced with a thiophilic metal selected from the group consisting of a thiophilic noble metal and a thiophilic semiconductive material.

In one embodiment the thiophilic metal used in a method according to the present disclosure is a noble metal selected from the group consisting of copper, silver and gold. In one embodiment the thiophilic metal is chosen from silver or gold. In one embodiment gold is used as thiophilic solid phase material. In one embodiment silver is used as thiophilic solid phase material.

In an exemplary embodiment the thiophilic semiconductor material used in a method according to the present disclosure for production of an oligonucleotide-solid phase conjugate is selected from cadmium or gallium. In some embodiments the semiconductor material used in a method according to the present disclosure for production of an oligonucleotide-solid phase conjugate is cadmium.

In one embodiment the thiophilic semiconductor material used in a method according to the present disclosure for production of an oligonucleotide-solid phase conjugate is present in form of a nano crystal or quantum dot.

In an embodiment the method according to the present disclosure for production of an oligonucleotide-solid phase conjugate is practiced with an oligonucleotide comprising at least one nucleotide with a nucleobase according to Formula I wherein said oligonucleotide is at least 8 nucleotides in length.

In an embodiment the method according to the present disclosure for production of an oligonucleotide-solid phase conjugate is practiced with an oligonucleotide comprising at least one nucleotide with a nucleobase according to Formula I wherein said oligonucleotide is at most 1000 nucleotides in length.

An oligonucleotide-solid phase conjugate as described in the present disclosure can be used for many quite important purposes.

For example, an oligonucleotide-solid phase conjugate as described in the present disclosure in one embodiment is used in a detection method based on nucleic acid hybridization. Such use is of paramount importance for multiplex applications or in biosensor, for example.

In one embodiment the solid phase in an oligonucleotide-solid phase conjugate as described in the present disclosure is a nanoparticle selected from the group consisting of a gold nanoparticle and thiophilic semiconductive material present as a nanocrystal and is used as a label. Such use is analogous to the uses e.g. described for electrochemical detection of hybridization (Kafka, J. et al., Electrochimica Acta 53 (2008) 7467-7474) or for detection with surface plasmon resonance (Milkani, E. et al., Biosensors & Bioelectronics 25 (2010) 1217-1220).

An oligonucleotide wherein the thiooxonucleobase of Formula I is a 6-deaza-thiooxonucleotide, can be easily synthesized, is stable against any nucleophilic attack.

The following examples, illustrative embodiments, and figures are provided for the purpose of demonstrating various embodiments of the instant disclosure and aiding in an understanding of the present disclosure, the true scope of which is set forth in the appended claims. These examples are not intended to, and should not be understood as, limiting the scope or spirit of the instant disclosure in any way. It should also be understood that modifications can be made in the procedures set forth without departing from the spirit of the disclosure

ILLUSTRATIVE EMBODIMENTS

The following comprises a list of illustrative embodiments according to the instant disclosure which represent various embodiments of the instant disclosure. These illustrative embodiments are not intended to be exhaustive or limit the disclosure to the precise forms disclosed, but rather, these illustrative embodiments are provided to aide in further describing the instant disclosure so that others skilled in the art may utilize their teachings.

1. An oligonucleotide-solid phase conjugate, wherein the solid phase comprises a thiophilic metal, wherein the oligonucleotide comprises at least one thiooxonucleobase according to Formula I,

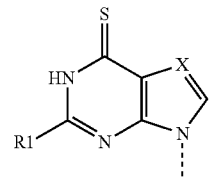

wherein X is CH or N, wherein R1 is H or NH2, wherein --- indicates a covalent bond, and wherein said oligonucleotide is bound to said solid phase via the sulphur atom of said thiooxonucleotide.

2. The oligonucleotide-solid phase conjugate of embodiment 1, wherein X in Formula I is CH.
3. The oligonucleotide-solid phase conjugate of embodiments 1 or 2, wherein the thiophilic solid phase is selected from the group consisting of a thiophilic noble metal or a semiconductor nanocrystal comprising a thiophilic metal.
4. The oligonucleotide-solid phase conjugate of embodiments 1 to 3, wherein the thiophilic solid phase is a noble metal selected from the group consisting of gold and silver.
5. The oligonucleotide-solid phase conjugate of embodiment 4, wherein the metal is gold.
6. The oligonucleotide-solid phase conjugate of embodiments 1 to 4, wherein the solid phase is a gold nanoparticle.
7. The oligonucleotide-sold phase conjugate of embodiment 4 wherein the metal is gold present as a layer on a solid support.
8. The oligonucleotide-solid phase conjugate of embodiment 1, wherein the thiophilic solid phase is a thiophilic semiconductive material.
9. The oligonucleotide-solid phase conjugate of embodiment 8, wherein the thiophilic semiconductive material is present as a nanocrystal.
10. The oligonucleotide-solid phase conjugate of embodiments 1 to 9, wherein the oligonucleotide is at least 8 nucleotides in length.
11. A method of producing an oligonucleotide-solid phase conjugate, the method comprising the steps of:
a) providing solid phase comprising a thiophilic metal; and
b) binding an oligonucleotide containing at least one thiooxonucleobase according to Formula I,

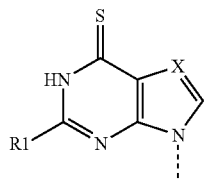

wherein X is CH or N, wherein R1 is H or NH2 and wherein --- indicates a covalent bond; to said thiophilic metal.
12. The method of embodiment 11, wherein in the oligonucleotide the thiooxonucleotide based on a nucleoside of Formula I is a 7-deazanucleotide, i.e., wherein X is CH.
13. The method of embodiment 11 or 12, wherein the oligonucleotide is at least 8 nucleotides in length.
14. Use of an oligonucleotide-solid phase conjugate according to any of embodiments 1 to 10 in a detection method based on nucleic acid hybridization.
15. Use of an oligonucleotide nanoparticle conjugate of embodiment 6 or 9 as a label.

EXAMPLES

General Information on Methods and Reagents

All chemicals were purchased from Acros, Fluka or Sigma-Aldrich (Sigma-Aldrich Chemie GmbH, Deisenhofen, Germany). The 5'-mercapto modifier 6-(triphenylmethyl)-S—(CH$_2$)$_6$ O-2-cyanoethyl diisopropylphosphoramidite was obtained from Glen Research (Virginia, USA). Solvents were of laboratory grade. Thin layer Chromatography (TLC) was carried out on aluminium sheets covered with silica gel 60 F254, 0.2 mm layer (0.2 mm; Merck, Darmstadt, Germany). Column flash chromatography (FC) was performed at 0.4 bar on silica gel 60 H (VWR, Darmstadt, Germany). UV-Vis spectra: U3200 spectrophotometer (Hitachi, Japan); $\lambda_{max}$ in nm, $\epsilon$ in dm$^3$ mol$^{-1}$. Reversed-phase HPLC was carried out on a 250×4 mm PR-18 column (Merck) with a Merck-Hitachi HPLC pump (model L-6250) connected with a variable wavelength monitor (model 655A). NMR Spectra: Avance-DPX-300 spectrometer (Bruker, Rheinstetten, Germany); chemical shifts ($\delta$) are in ppm rel. to internal SiMe$_4$ ($^1$H, $^{13}$C). MALDI-TOF mass spectra were recorded with Applied Biosystems Voyager DE PRO spectrometer with 3-hydroxypicolinic acid (3-HPA) as a matrix. Microanalyses were performed by Mikroanalytisches Labor Beller (Göttingen, Germany). The melting temperature curves were measured with a Cary-100 Bio UV-VIS spectrophotometer (Varian, Australia) equipped with a Cary thermoelectrical controller. Nanopure water (resistance<0.055 µS/cm) from Membra-Pure water system (Astacus) was used for all experiments.

Example 1

Oligonucleotides with Thio Substituents 1.1 Building Block Synthesis

Figure 2:
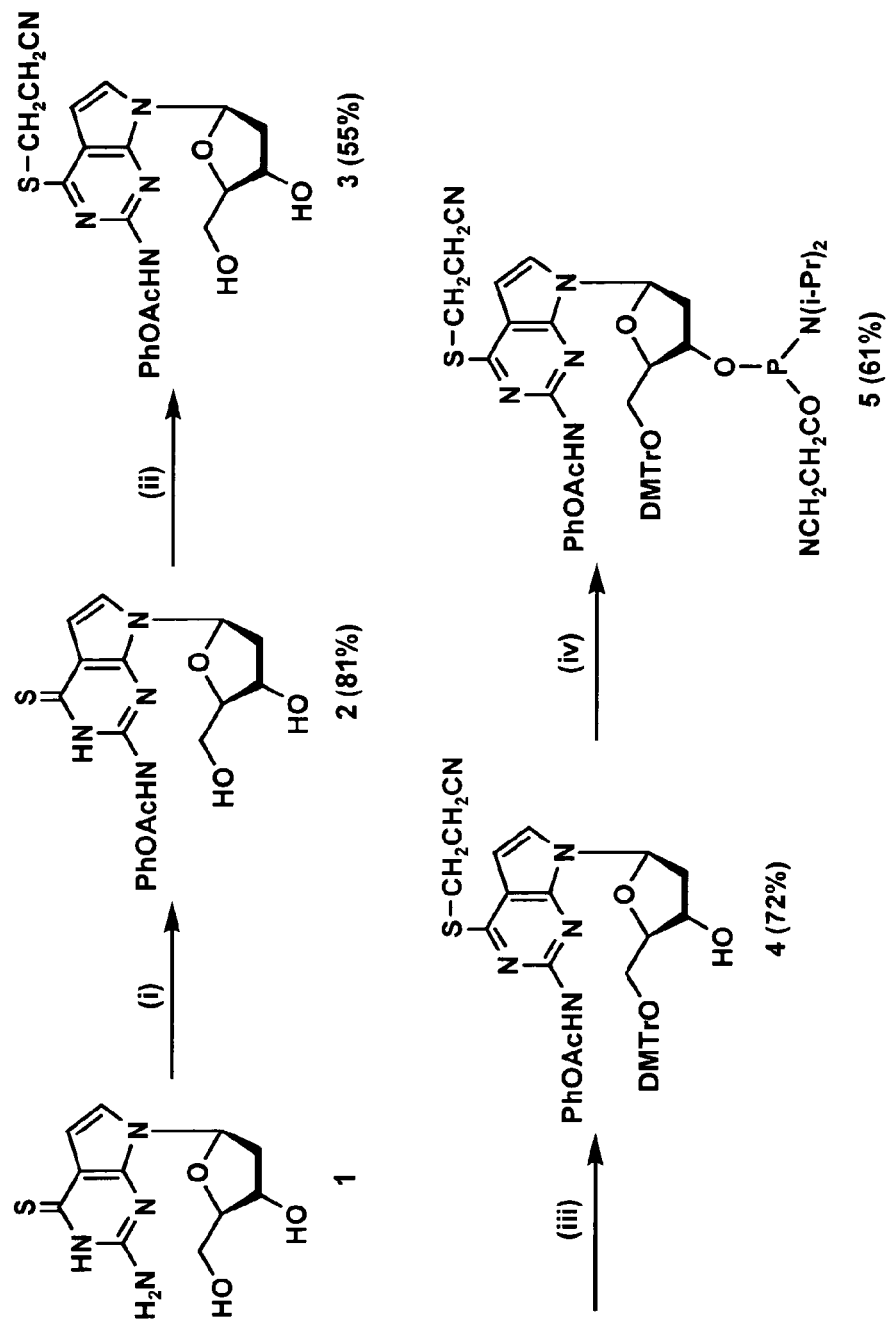
FIG. 2 is a schematic of steps in the synthesis of building block for chemical synthesis of an oligonucleotide based on 7 deaza 6 thio guanosine.

The building block synthesis is schematically exemplified in FIG. 2 and Scheme 2, below.

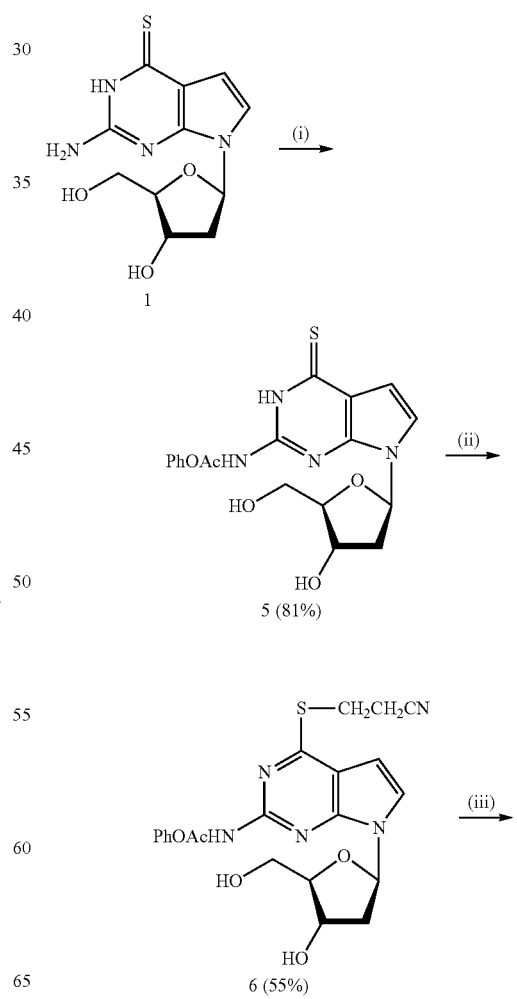

-continued

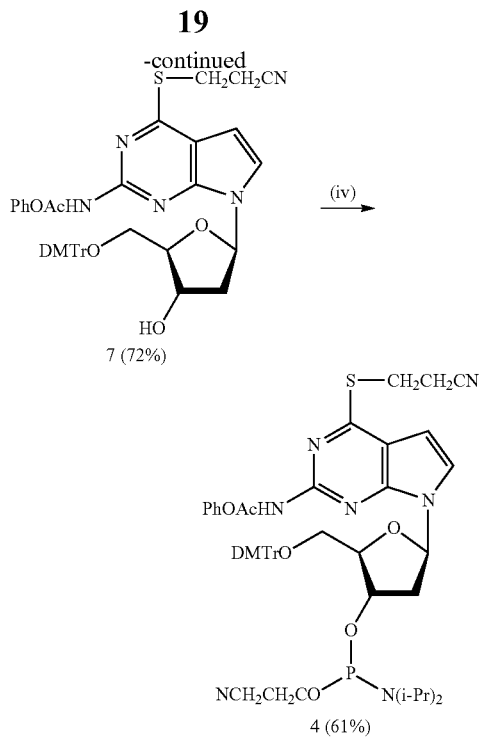

Scheme 2

Reagents and conditions: (i) Me$_3$SiCl, phenoxyacetyl chloride, pyridine, aq. NH$_3$, 4 h, r.t.; (ii) 3-bromopropionitrile, anh. K$_2$CO$_3$, DMF, overnight, r.t.; (iii) DMTr-Cl, pyridine, 3 h, r.t.; (iv) (2-cyanoethyl)diisopropylphosphoramido chloridite, N,N-diisopropylethylamine, anh. CH$_2$Cl$_2$, 20 min, r.t.

7-(2-Deoxy-β-D-erythro-pentofuranosyl)-2-phenoxyacetamino-7H-pyrrolo[2,3-c]pyrimidin-4(3H)-thione (2)

Compound 1 (1.6 g, 5.50 mmol) was coevaporated with dry pyridine (3×8.0 ml) then suspended in pyridine (15 ml). Trimethylsilyl chloride (3.6 ml, 28.17 mmol) was added via a dry syringe and the reaction was stirred for 1 hour. Phenoxyacetyl chloride (1.1 ml, 7.96 mmol) was added via a dry syringe and the reaction was allowed to stir at room temperature for 4 hours. The reaction vessel was cooled in an ice bath and water (5 ml) was added while stirring. After 15 min, conc. aq. ammonia (5 ml) was added and the slurry was stirred for an additional 15 min. The solvent was evaporated, and the residue was applied to FC (silica gel, column 8×15 cm, CH$_2$Cl$_2$/MeOH, 50:1→25:1). The main zone was evaporated to give 2 as a colourless foam (1.9 g, 80.9%); mp 205° C.; R$_f$=0.53 (CH$_2$Cl$_2$/MeOH, 9:1). UV (MeOH): λ$_{max}$ (ε)=333 nm (47600). $^1$H NMR (300 MHz, DMSO-d$_6$): δ=2.15-2.22 (m, 1H, H$_\alpha$-2'), 2.38-2.47 (m, 1H, H$_\beta$-2'), 3.52 (m, 2H, H-5'), 3.82 (m, 1H, H-4'), 4.35 (m, 1H, H-3'), 4.88 (s, 2H, Pac-CH$_2$), 4.95 (t, $^3$J(H,H)=5.3 Hz, 1H, 5'-OH), 5.30 (d, $^3$J(H,H)=3.6 Hz, 1H, 3'-OH), 6.41 (m, 1H, H-1'), 6.64 (d, $^3$J(H,H)=3.7 Hz, 1H, H-5), 6.96-7.00 (m, 3H, phenoxy), 7.28-7.34 (m, 2H, phenoxy), 7.49 (d, $^3$J(H,H)=3.7 Hz, 1H, H-6), 11.99 (s, br, 1H, N—H), 12.88 (s, br, 1H, CO—NH). Anal. Calcd. for C$_{19}$H$_{20}$N$_4$O$_5$S (416.45): C, 54.80; H, 4.84; N, 13.45. Found: C, 54.74; H, 4.90; N, 13.40.

4-[(2-Cyanoethyl)thio]-7-(2-deoxy-β-D-erythro-pentofuranosyl)-2-phenoxyacetamino-7H-pyrrolo[2,3-d]pyrimidine (3)

3-Bromopropionitrile (4.0 ml, 48.07 mmol) and anhydrous K$_2$CO$_3$ (3.0 g, 21.71 mmol) were added to 25 ml dry dimethylformamide (DMF) and the mixture was stirred vigorously. Compound 2 (1.9 g, 4.45 mmol) was dissolved in 5 ml dry DMF and added dropwise to the stirred solution within 30 min. The mixture was kept on stirring overnight. The DMF was removed by coevaporation with xylene and the residue was applied to FC (silica gel, column 8×15 cm, CH$_2$Cl$_2$/MeOH, 500:1→100:1). After evaporation, the main zone yielded 3 as a colourless solid (1.2 g, 54.7%); R$_f$=0.22 (CH$_2$Cl$_2$/MeOH, 95:5). UV (MeOH): λ$_{max}$ (ε)=301 nm (26700); 244 nm (73300). $^1$H NMR (300 MHz, DMSO-d$_6$): δ=2.22 (m, 1H, H$_\alpha$-2'), 2.50 (m, 1H, H$_\beta$-2'), 3.16 (t, 2H, CH$_2$—CN), 3.51-3.56 (m, 4H, H-5', H-5", CH$_2$—S), 3.84 (m, 1H, H-4'), 4.37 (m, 1H, H-3'), 4.94 (t, $^3$J(H,H)=5.4 Hz, 1H, 5'-OH), 5.00 (s, 2H, Pac-CH$_2$), 5.32 (d, $^3$J(H,H)=5.3 Hz, 1H, 3'-OH), 6.55 (m, 2H, H-5, H-1'), 6.95 (m, 3H, phenoxy), 7.31 (m, 2H, phenoxy), 7.65 (d, $^3$J(H,H)=3.9 Hz, 1H, H-6), 10.69 (s, 1H, CO—NH). Anal. Calcd. for C$_{22}$H$_{23}$N$_5$O$_5$S (469.51): C, 56.28; H, 4.94; N, 14.92. Found: C, 56.18; H, 4.98; N, 14.89.

4-[(2-Cyanoethyl)thio]-7-[2-deoxy-5-O-(4,4'-dimethoxytrityl)-β-D-erythro-pentofuranosyl]-2-phenoxyacetamino-7H-pyrrolo[2,3-d]pyrimidine (4)

Compound 6 (469.5 mg, 1.00 mmol) was co-evaporated with anhydrous pyridine (3×5.0 ml) and then dissolved in pyridine (5.0 ml). To this solution, 4,4'-dimethoxytriphenylmethyl chloride (DMT-Cl) (440.5 mg, 1.30 mmol) was added and the mixture was stirred at r.t. for 3 h. The reaction was quenched by the addition of MeOH and the mixture was evaporated to dryness. The mixture was dissolved in CH$_2$Cl$_2$ (3.0 ml) and subjected to FC (column 4×10 cm, elution with CH$_2$Cl$_2$/acetone, 20:1) to give 4 as a colourless foam (555.8 mg, 72%); R$_f$=0.61 (CH$_2$Cl$_2$/MeOH, 95:5). UV (MeOH): λ$_{max}$ (ε)=302 nm (14400); 240 nm (53500). $^1$H NMR (300 MHz, DMSO-d$_6$): δ=2.29 (m, 1H, H$_\alpha$-2'), 2.59 (m, 1H, H$_\beta$-2'), 3.16 (m, 4H, CH$_2$—CN, H-5', H-5"), 3.54 (m, 2H, CH$_2$—S), 3.71 (s, 6H, OCH$_3$), 3.95 (m, 1H, H-4'), 4.37 (m, 1H, H-3'), 5.00 (s, 2H, Pac-CH$_2$), 5.37 (d, $^3$J(H,H)=4.2 Hz, 1H, 3'-OH), 6.52-6.56 (m, 2H, H-5, H-1'), 6.78-7.35 (m, 18H, phenoxy), 7.46 (d, $^3$J(H,H)=3.6 Hz, 1H, H-6), 10.69 (s, 1H, CO—NH). Anal. calcd for C$_{43}$H$_{41}$N$_5$O$_7$S (771.27): C, 66.91; H, 5.35; N, 9.07. Found: C, 67.05; H, 5.20; N, 9.17.

4-[(2-Cyanoethyl)thio]-7-[2-deoxy-5-O-(4,4'-dimethoxytrityl)-β-D-erythro-pentofuranosyl]-2-phenoxyacetamino-7H-pyrrolo[2,3-d]pyrimidine 3'-[(2-cyanoethyl)-N,N-diisopropylphosphoramidite] (5)

Compound 4 (555.8 mg, 0.72 mmol) was dissolved in anhydrous CH$_2$Cl$_2$ (3.0 ml) under Ar and was reacted with (2-cyanoethyl)diisopropylphosphoramido chloridite (225 μl, 0.95 mmol) in the presence of $^i$Pr$_2$EtN (220 μl, 1.27 mmol) at room temperature. After 20 min, the reaction mixture was diluted with CH$_2$Cl$_2$ and the solution was washed with a 5% aqueous NaHCO$_3$ solution, followed by brine. The organic solution was dried over anhydrous Na$_2$SO$_4$, filtrated and concentrated. The residue was submitted to FC (column 4×10 cm, CH$_2$Cl$_2$/acetone, 25:1) yielding 5 as a colourless foam (429.1 mg, 61.3%); R$_f$=0.64 (CH$_2$Cl$_2$/acetone, 95:5). $^{31}$P NMR (300 MHz, CDCl$_3$-d$_6$): δ=148.6; 148.7.

All compounds were characterized by UV-spectra, $^1$H- and $^{13}$C-NMR spectra as well as by elemental analysis (Table 1 and experimental part). The assignments of $^{13}$C NMR chemical shifts of the sugar moiety and the protecting groups was made on the basis of gated-decoupled spectra in combination with already published data (Christopherson, M. S, and Broom, A. D., Nucleic Acids Res. 19 (1991) 5719-5724).

TABLE 1

$^{13}$C-NMR Chemical Shifts (δ) of 6-Thio-7-deaza-2'-deoxyguanosine Derivatives.$^a$

| Compd | C(2)$^b$ C(2)$^c$ | C(4)$^b$ C(6)$^c$ | C(4a)$^b$ C(5)$^c$ | C(5)$^b$ C(7)$^c$ | C(6)$^b$ C(8)$^c$ | C(7a)$^b$ C(4)$^c$ | C(1') | C(2') | C(3') | C(4') | C(5') |
|---|---|---|---|---|---|---|---|---|---|---|---|
| 1 | 152.2 | 175.7 | 113.1 | 104.4 | 120.2 | 147.1 | 82.2 | —$^d$ | 71.0 | 87.1 | 61.9 |
| 2 | 145.4 | 174.8 | 116.8 | 104.7 | 122.7 | 143.4 | 82.5 | —$^d$ | 70.6 | 87.1 | 61.5 |
| 3 | 151.0 | 167.3 | 119.5 | 99.5 | 125.0 | 149.2 | 82.6 | —$^d$ | 70.9 | 87.4 | 61.8 |
| 4 | 151.2 | 167.3 | 99.5 | 112.3 | 120.9 | 149.2 | 82.8 | —$^d$ | 67.2 | 85.5 | 55.1 |

$^a$Measured in DMSO-d$_6$ at 298 K.
$^b$Systematic numbering.
$^c$Purine numbering.
$^d$Superimposed by the DMSO signal.

1.2 Oligonucleotide Synthesis, Purification and Characterization of the Oligonucleotides 1.2.1 Synthesis of Oligonucleotides The oligonucleotides were synthesized in an automated DNA Synthesizer, model 392-08 (ABI 392, Applied Biosystems, Weiterstadt, Germany) at 1 μmol scale employing standard phosphoramidites as well as the phosphoramidite 5 according to the standard procedure for solid phase synthesis of oligonucleotides as described earlier (Seela, F., Budow, S., Helv. Chim. Acta 89 (2006) 1978-1985). After cleavage from the solid support, the oligonucleotides were deprotected in 25% aqueous ammonia solution for 12-16 h at 60° C.

1.2.2 Purification of Oligonucleotides

The purification of the oligonucleotides containing the thionucleoside 1 was firstly carried out on reversed-phase HPLC in the DMT-on modus (Merck-Hitachi-HPLC; RP-18 column; gradient system [A: 0.1 M (Et$_3$NH)OAc (pH 7.0)/MeCN 95:5; B: MeCN]: 3 min, 20% B in A, 12 min, 20-50% B in A and 25 min, 20% B in A with a flow rate of 1.0 ml/min. The solutions were dried and treated with 2.5% CHCl$_2$COOH—CH$_2$Cl$_2$ (400 μl) for 5 min at 0° C. to remove the 4,4'-dimethoxytrityl residues. The detritylated oligomers were purified again by reversed-phase HPLC [gradient: 0-20 min 0-20% B in A; flow rate 1 ml/min]. The oligomers were desalted on a short column (RP-18, silica gel) and lyophilized on a Speed-Vac evaporator to yield colorless solids which were frozen at −24° C. HPLC (gradient: 0-25 min 0-20% A in B; flow rate 1.0 ml/min).

1.2.3 Characterization of the Oligonucleotides by Mass Spectrometry

MALDI-TOF mass spectra were recorded with Applied Biosystems Voyager DE PRO spectrometer with 3-hydroxypicolinic acid (3-HPA) as a matrix.

The oligonucleotides were characterized after complete deprotection and HPLC purification, followed by desalting. In all cases, the calculated masses were in good agreement with the measured values (Table 2).

TABLE 2

Oligonucleotides used in this study and molecular masses determined by MALDI-TOF mass spectrometry.

| | [M − H]$^-$ (Da) | |
|---|---|---|
| Oligonucleotide | Calc. | Found |
| 5'-d(AGT ATT GAC CTA A1T ATT GAC CTA) (6) (SEQ ID. NO. 1) | 7365 | 7364 |

TABLE 2-continued

Oligonucleotides used in this study and molecular masses determined by MALDI-TOF mass spectrometry.

| | [M − H]$^-$ (Da) | |
|---|---|---|
| Oligonucleotide | Calc. | Found |
| 5'-d(AGT ATT 1AC CTA) (7) (SEQ ID. NO. 2) | 3660 | 3659 |
| 5'-d(1-T$_{10}$-TAG GTC AAT ACT) (8) (SEQ ID. NO. 5) | 7030 | 7030 |
| 5'-d(1-T$_{10}$-AGT ATT GAC CTA) (9) (SEQ ID. NO. 6) | 7030 | 7030 |

Spacer T$_{10}$ = TTT TTT TTT T.

1.2.4 Characterization of the Oligonucleotides by Enzymatic Digestion

Figure 3:
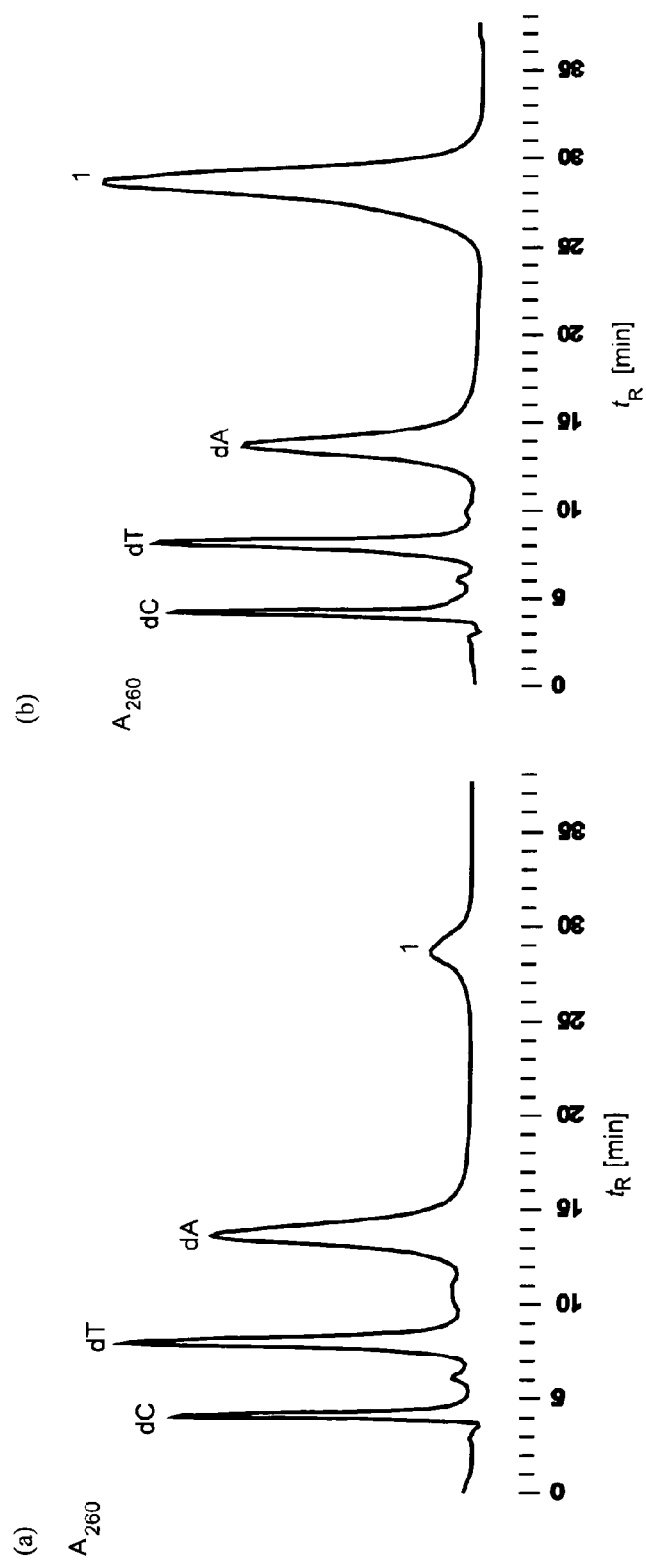
FIG. 3a is a graph showing the HPLC elution profile of the enzymatic hydrolysis products of oligonucleotide 7 obtained after enzymatic digestion.
FIG. 3b is a graph showing the HPLC elution profile of an artificial mixture comprising the theoretically expected hydrolysis products of oligonucleotide 7 and thionucleoside 1.

The enzymatic hydrolysis of the oligonucleotides was performed as described by Seela and Becher (Seela, F., Becher, G., Nucleic Acids Res. 29 (2001) 2069-2078) with snake-venom phosphodiesterase (EC 3.1.15.1, *Crotallus adamanteus*) and alkaline phosphatase (EC 3.1.3.1, *Escherichia coli* from Roche Diagnostics GmbH, Germany) in 0.1 M Tris-HCl buffer (pH 8.5) at 37° C. and was carried out on reversed-phase HPLC. HPLC elution profiles of (a) the enzymatic hydrolysis products of oligonucleotide 7 obtained after enzymatic digestion and (b) the artificial mixture of the theoretically expected hydrolysis products of oligonucleotide 7 and thionucleoside 1 are shown in FIG. 3. Column and elution conditions were: RP-18 (200×10 mm); gradient [A: 0.1 M (Et₃NH)OAc (pH 7.0)/MeCN 95:5; B: MeCN]: 25 min. A, 40 min. 0-65% B in A for (a) and (b); 100% A for (c) and (d); flow rate: 0.7 ml/min.

As obvious from comparison of FIG. 3 (*a*) and FIG. 3 (*b*), respectively, snake venom phosphodiesterase does not cleave of the thionucleotide 1.

Example 2

Synthesis of Modified Gold Nanoparticles and their Characterization 2.1 Preparation of the Gold Nanoparticle Solution The 15 nm gold nanoparticle solutions were prepared from a HAuCl₄ solution by citrate reduction as it was originally reported in Turkevich, J. et al., Discuss. Faraday Soc. 11 (1951) 55 and later described by Letsinger and Mirkin (Storhoff, J. J. et al., J. Am. Chem. Soc. 120 (1998) 1959-1964, and Jin, R. et al., J. Am. Chem. Soc. 125 (2003) 1643). All glassware was cleaned in aqua regia (3 parts HC1,1 part HNO₃), rinsed with nanopure water, then oven dried before use. Aqueous HAuCl₄ (1 mM, 250 ml) was brought to reflux while stirring. Then, 38.8 mM tri-sodium citrate (25 ml) was added quickly. The solution colour changed from yellow to red, and refluxing was continued for 15 min. After cooling to room temperature, the red solution was filtered through a Micron Separations Inc. 1 micron filter.

2.2 Preparation of the Modified Gold Nanoparticle Solution Using Oligonucleotides Employing the Nucleoside 1

The gold nanoparticles (~6 nM) were functionalized with various oligonucleotides containing nucleoside 1 at different positions within their sequence. The DNA-AuNPs conjugates were prepared by mixing 1 ml of the gold nanoparticle solution with purified oligonucleotide solutions (final oligonucleotide concentration of 3 µM). The coupling reaction was performed at slightly elevated temperature (40° C.). After standing for 20 h, 5 µl of a 2 M NaCl, 0.2 mM phosphate buffer solution (pH 7.0) were added under constant stirring to bring the colloid solution to 0.01 M of NaCl, standing for 6-8 h. Colloids were next salted to 0.02 M and allowed to age for another 6-8 h, were then salted to 0.05 M for standing 6-8 h, and were finally salted to 0.1 M NaCl. Subsequently, the DNA gold nanoparticle solutions were centrifuged and the clear supernatant was taken off to remove unbound oligonucleotides. The precipitate was redispersed in 1 ml of a 0.1 M NaCl, 10 mM phosphate buffer solution (pH 7.0). After incubation (24 h, 40° C.) the conjugate solutions were washed again with same buffer, finally yielding 1 ml of the DNA-AuNPs conjugate.

Example 3

Hybridization of DNA-Gold Nanoparticle Conjugates Employing Thionucleoside 1 as a Linker In a typical experiment, 0.5 ml of 0.1 M NaCl, 10 mM phosphate, pH 7 buffer solution containing the DNA-AuNP conjugate and 0.5 ml of 0.1 M NaCl, 10 mM phosphate, pH 7 buffer solution containing the DNA-AuNP conjugate with the complementary oligonucleotide were mixed together (equal concentrations). The solution containing both DNA-AuNP conjugates was allowed to incubate overnight. During this, slow hybridization of the complementary oligonucleotide AuNP conjugates occurred evidenced by slow red shifting and broadening of the plasmon resonance band concomitant by a red to purple colour change. Finally, precipitation of the DNA gold nanoparticle network is observed resulting in a clear supernatant and a dark precipitate. After intensive shaking of the DNA-AuNP solution, the precipitate can be re-dispersed leading to a purple solution with an UV/VIS maximum of around 564 nm.

Example 4

Immobilization of Oligonucleotides on Gold Surfaces 4.1 Oligonucleotide Hybridization Hybridization properties of oligonucleotide duplexes employing thionucleoside 1 in solution. In principle any position within the oligonucleotide sequence can be selected when 7-deaza-6-thio-2'-deoxyguanosine (1) is used as anchor group for binding of an oligonucleotide to a gold nanoparticle. Therefore several different modification sites have been selected for incorporation. It is well known that the bulkiness of the sulphur atom can interfere with hybridization. For clarification, hydridization studies were performed with free oligonucleotides incorporating compound 1. A single replacement of nucleoside 1 in the centre or at the periphery of the 12-mer duplex reduced the stability of the duplex compared to the parent unmodified duplex 5'-d(TAG GTC AAT ACT) (10)•3'-d(ATC CAG TTA TGA) (11) (Table 3). The effect is more pronounced when 1 is incorporated in the centre of the oligonucleotide duplex (10•7: $\Delta T_m = -7°$ C.) than at the periphery (10•12: $\Delta T_m = -3°$ C.). Multiple modifications lead to significant further destabilization ($\Delta T_m = -30°$ C. for 13•14) (Table 3). Consistently, the incorporation of two thionucleosides (1) within the center or at the periphery of 24-mer duplexes (21•22, 23•6) affects a strong decrease of the duplex stability when compared to the parent unmodified duplex (19•20). Contrary, in duplex 8•9, 15•16 and 17•18 containing one or multiple incorporations of thionucleoside 1 as overhanging ends, no destabilisation of the duplex was observed.

TABLE 3

$T_m$ values and thermodynamic data of oligonucleotide duplexes containing nucleoside 1 opposite to canonical nucleosides or as overhanging ends.[a]

| Duplex | $T_m$ [° C.] | $\Delta T_m^b$ [° C.] |
|---|---|---|
| 5'-d(TAG GTC AAT ACT) (10) (SEQ ID. NO. 5) 3'-d(ATC CAG TTA TGA) (11) (SEQ ID. NO. 6) | 47 | — |
| 5'-d(TAG GTC AAT ACT) (10) (SEQ ID. NO. 5) 3'-d(ATC CA1 TTA TGA) (7) (SEQ ID. NO. 2) | 40 | −7 |

TABLE 3-continued

T$_m$ values and thermodynamic data of oligonucleotide duplexes containing nucleoside 1 opposite to canonical nucleosides or as overhanging ends.[a]

| Duplex | T$_m$ [° C.] | ΔT$_m$[b] [° C.] |
|---|---|---|
| 5'-d(TAG GTC AAT ACT) (10) (SEQ ID. NO. 5) 3'-d(ATC CAG TTA T1A) (12) (SEQ ID. NO. 7) | 44 | −3 |
| 5'-d(TA1 1TC AAT ACT) (13) (SEQ ID. NO. 8) 3'-d(ATC CA1 TTA T1A) (14) (SEQ ID. NO. 9) | 17 | −30 |
| 5'-d(1 T$_{10}$ TAG GTC AAT ACT) (8) (SEQ ID. NO. 3) 3'-d(ATC CAG TTA TGA T$_{10}$ 1) (9) (SEQ ID. NO. 4) | 48 | +1 |
| 5'-d(11 T$_{10}$ TAG GTC AAT ACT) (15) (SEQ ID. NO. 10) 3'-d(ATC CAG TTA TGA T$_{10}$ 11) (16) (SEQ ID. NO. 11) | 47 | 0 |
| 5'-d(111 T$_{10}$ TAG GTC AAT ACT) (17) (SEQ ID. NO. 12) 3'-d(ATC CAG TTA TGA T$_{10}$ 111) (18) (SEQ ID. NO. 13) | 47 | 0 |
| 5'-d(TAG GTC AAT ACT TAG GTC AAT ACT) (19) (SEQ ID. NO. 14) 3'-d(ATC CAG TTA TGA ATC CAG TTA TGA) (20) (SEQ ID. NO. 15) | 65 | — |
| 5'-d(TA1 GTC AAT ACT TAG GTC AAT ACT) (21) (SEQ ID. NO. 16) 3'-d(ATC CAG TTA TGA ATC CAG TTA T1A) (22) (SEQ ID. NO. 17) | 55 | −10 |
| 5'-d(TAG GTC AAT ACT TA1 GTC AAT ACT) (23) (SEQ ID. NO. 18) 3'-d(ATC CAG TTA T1A ATC CAG TTA TGA) (6) (SEQ ID. NO. 1) | 53 | −12 |

[a]Measured at 260 nm in 0.1 M NaCl, 10 mM phosphate buffer (pH 7.0) with 5 µM single-strand concentration.
[b]ΔT$_m$ was calculated as T$_m^{base\ mismatch}$ − T$_m^{base\ match}$.
Spacer T$_{10}$ = TTT TTT TTT T.

4.2 Preparation of Oligonucleotide Gold Nanoparticle Conjugates

A 15 nm gold nanoparticle solution was prepared from a HAuCl$_4$ solution by citrate reduction according to the protocol reported by Turkevich and later described by Letsinger and Mirkin (Elghanian, R., et al., Science 277 (1997) 1078-1081; Mirkin, C. A. et al., Nature 283 (1996) 607-609; Turkevich, J. et al., Discuss. Faraday Soc. 11 (1951) 55). The nanoparticle concentration was determined to be approximately 6.0 nM, using $\epsilon_{520}$=4.2×10$^8$ M$^{−1}$ cm$^{−1}$ (UV/VIS$_{max}$: 520 nm) (Demers, L. M. et al., Anal. Chem. 72 (2000) 5535-5541). The UV/VIS spectrum of the unmodified gold nanoparticle solution is shown in FIG. 4a. The unmodified AuNPs were functionalized with oligonucleotides shown in Table 4.

TABLE 4

Single-stranded oligonucleotides used for conjugation to AuNPs.

| Oligonucleotides |
|---|
| 5'-d(1 T$_{10}$ TAG GTC AAT ACT) (8) (SEQ ID. NO. 5) |
| 5'-d(1 T$_{10}$ AGT ATT GAC CTA) (9) (SEQ ID. NO. 6) |
| 5'-d(11 T$_{10}$ TAG GTC AAT ACT) (15) (SEQ ID. NO. 10) |
| 5'-d(11 T$_{10}$ AGT ATT GAC CTA) (16) (SEQ ID. NO. 11) |

TABLE 4-continued

Single-stranded oligonucleotides used for conjugation to AuNPs.

Oligonucleotides

5'-d(1l1 T$_{10}$ TAG GTC AAT ACT) (17)
(SEQ ID. NO. 12)

5'-d(1l1 T$_{10}$ AGT ATT GAC CTA) (18)
(SEQ ID. NO. 13)

5'-d(TA1 GTC AAT ACT TAG GTC AAT ACT) (21)
(SEQ ID. NO. 16)

5'-d(A1T ATT GAC CTA AGT ATT GAC CTA) (22)
(SEQ ID. NO. 17)

5'-d(TAG GTC AAT ACT TA1 GTC AAT ACT) (23)
(SEQ ID. NO. 18)

5'-d(AGT ATT GAC CTA A1T ATT GAC CTA) (6)
(SEQ ID. NO. 1)

5'-d(Trityl-S—(CH$_2$)$_6$-T$_{10}$ TAG GTC AAT ACT) (24)
(SEQ ID. NO. 19)

5'-d(Trityl-S—(CH$_2$)$_6$-T$_{10}$ AGT ATT GAC CTA) (25)
(SEQ ID. NO. 20)

Spacer T$_{10}$ = TTT TTT TTT T.

Figure 4:
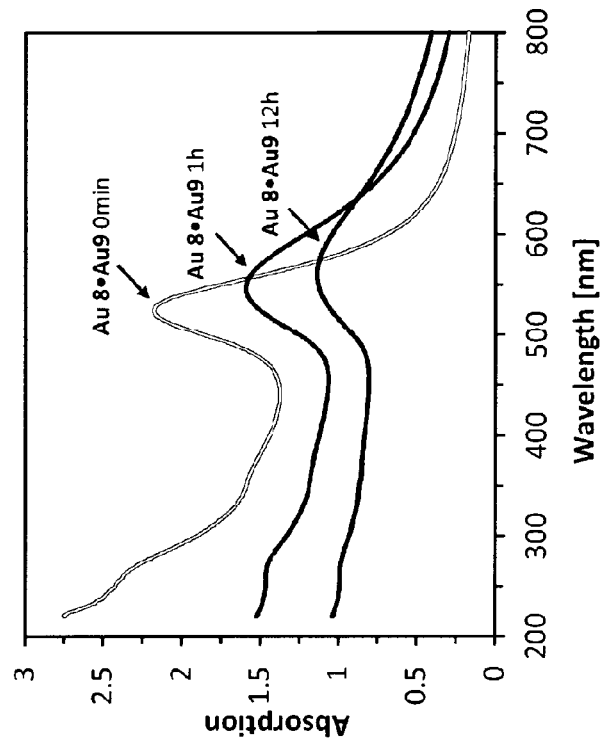
FIG. 4a is a UV-VIS spectra of the unmodified AuNP solution (top line, starting from the left end), DNA-AuNP conjugate Au8 employing thionucleoside 1 (medium line) and DNA-AuNP conjugate Au24 containing a thiolhexyl linker (bottom line).
FIG. 4b is a UV-VIS spectra of DNA-AuNP conjugates Au8•Au9 carrying complementary oligonucleotides measured after different time intervals of 0 min, 4 h and 12 h, respectively.
Figure 4:
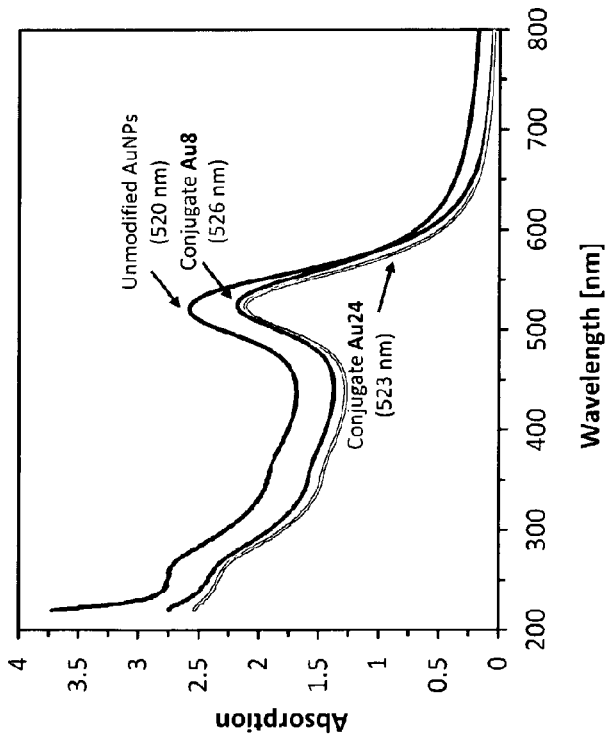

The DNA-AuNP conjugates Au8 and Au18 as well as Au21 and Au6, respectively, (Tables 3 and 4, respectively) were prepared by mixing 1 ml of the gold nanoparticle solution with the aq. solution of the purified oligonucleotide (1-5 µA to yield a final oligonucleotide concentration of 3 µM. The coupling reaction was performed at slightly elevated temperature (40° C.). After standing for 24 h, 5 µl of a 2 M NaCl, 0.2 mM phosphate buffer solution (pH 7.0) was added under constant stirring to bring the DNA-AuNP solution to a 0.01 M NaCl concentration. The NaCl concentration of the DNA-AuNP solution was stepwise increased with phosphate buffer (2 M NaCl, 0.2 mM phosphate buffer, pH 7.0) to a final NaCl concentration of 0.1 M. The DNA-AuNP conjugates were washed twice with a 0.1 M NaCl, 10 mM phosphate buffer (pH 7.0) to remove unbound oligonucleotides. Finally, the DNA-AuNP conjugates were dispersed in 1 ml of the 0.1 M NaCl, 10 mM phosphate buffer (pH 7.0). During the whole procedure the DNA gold nanoparticle solutions stayed deep red in colour. Moreover, the resulting DNA-AuNP conjugates Au8, Au18 and Au21, Au6, respectively, show the expected plasmon resonance at around 525 nm indicating a non-aggregated state (Table 5, FIG. 4a). For comparison, oligonucleotides 24 and 25 incorporating a 5'-hexylthiol linker were conjugated to AuNPs (→Au24, Au25, respectively, Table 5) employing the conventional protocol reported earlier by others (Hurst, S. J. et al., Anal. Chem. 78 (2006) 8313-8318; Seela, F. et al., Chem. Biodiv. 2 (2005) 84-91). The UV/VIS spectrum of the DNA-AuNP conjugate Au8 employing 1 as anchor molecule shows a plasmon resonance (526 nm) which is very close to that one observed for the conjugate Au24 (523 nm) using the commercially available hexylthiol linker as anchor group (FIG. 4).

It is interesting to note that the UV/VIS spectra recorded for DNA-AuNP conjugates Au21 and Au6, respectively, in which the oligonucleotides bind to the AuNPs through an interior position of the thionucleoside 1 are qualitatively identical to those observed for the DNA-AuNP conjugates Au8 and Au18 as well as Au24 and Au25, respectively with anchor molecules located at a terminal position (Table 5).

All DNA-AuNP conjugates were found to be stable in 0.1 M NaCl, 10 mM phosphate buffer solution (pH 7.0); no aggregation of the particles accompanied with shifting of the maximum of the UV/VIS was observed. This is an important property, since an unfunctionalized gold nanoparticle solution undergoes irreversible aggregation followed by precipitation in buffer solutions containing NaCl within a few minutes (Mirkin, C. A. et al., Nature 283 (1996) 607-609).

Both results, (i) the maximum of the UV/VIS at around 523-526 nm and (ii) the stability in a 0.1 M NaCl phosphate buffer solution, can be considered as strong proofs for the covalent attachment of oligonucleotides via 7-deaza-6-thio-2'-deoxyguanosine (1). Thereby any position of compound 1—at the 5'- or 3'-end of the oligonucleotide or in an internal position—allows the construction of stable DNA-AuNP conjugates.

TABLE 5

Gold nanoparticle conjugates comprising various types of oligonucleotides and the maximum of the UV/VIS absorption.

| Oligonucleotide Gold Nanoparticle Conjugates | Max. VIS Absorption [nm] |
|---|---|
| <br>5'-d(1 T$_{10}$ TAG GTC AAT ACT)(Au8)<br>(SEQ ID NO. 5) | 526 |
| <br>5'-d(1 T$_{10}$ AGT ATT GAC CTA)(Au9)<br>(SEQ ID NO. 6) | 525 |
| <br>5'-d(1l T$_{10}$ TAG GTC AAT ACT)(Au15)<br>(SEQ ID NO. 10) | 525 |

TABLE 5-continued

Gold nanoparticle conjugates comprising various types of oligonucleotides and the maximum of the UV/VIS absorption.

| Oligonucleotide Gold Nanoparticle Conjugates | Max. VIS Absorption [nm] |
|---|---|
| <br>5'-d(11 T$_{10}$ AGT ATT GAC CTA)(Au16)<br>(SEQ ID NO. 11) | 526 |
| <br>5'-d(111 T$_{10}$ TAG GTC AAT ACT)(Au17)<br>(SEQ ID NO. 12) | 526 |
| <br>5'-d(111 T$_{10}$ AGT ATT GAC CTA)(Au18)<br>(SEQ ID NO. 13) | 525 |
| <br>5'-d(TA1 GTC AAT ACT TAG GTC AAT ACT)(Au21)<br>(SEQ ID NO. 16) | 526 |
| <br>5'-d(A1T ATT GAC CTA AGT ATT GAC CTA)(Au22)<br>(SEQ ID NO. 17) | 525 |
| <br>5'-d(TAG GTC AAT ACT TA1 GTC AAT ACT)(Au23)<br>(SEQ ID NO. 18) | 525 |
| <br>5'-d(AGT ATT GAC CTA A1T ATT GAC CTA)(Au6)<br>(SEQ ID NO. 1) | 525 |
| <br>5'-d(S—(CH$_2$)$_6$-T$_{10}$ TAG GTC AAT ACT) (Au24)<br>(SEQ ID NO. 19) | 523 |
| <br>5'-d(S—(CH$_2$)$_6$-T$_{10}$ AGT ATT GAC CTA) (Au25)<br>(SEQ ID NO. 20) | 523 |

Spacer T$_{10}$ = TTT TTT TTT T.

4.3 Hybridization Experiments of Assembled DNA Gold Nanoparticle Conjugates

In this series of experiments, the hybridization properties of the DNA-AuNP conjugates incorporating thionucleoside 1 were investigated and compared to those obtained from DNA-AuNP conjugates carrying 5'-hexylthiol linkers. In a typical experiment, two DNA-AuNP conjugate probes carrying oligonucleotides with complementary sequences were mixed together (equal concentrations in 0.1 M NaCl, 10 mM phosphate, pH 7.0), e.g. DNA-AuNP conjugates Au8 and Au9. The mixture was allowed to incubate. During this, slow hybridization of the complementary oligonucleotides being attached to the gold nanoparticles occurred; evidenced by red shifting of the VIS maximum (Au8•Au9: 526 nm→546 nm) and broadening of the plasmon resonance band concomitant by a red to purple colour change (FIG. 4b). Finally, precipitation of the DNA gold nanoparticle network is observed resulting in a clear supernatant and a dark red precipitate. The hybridized sample is rather stable, it can be redispersed but stays purple even after intensive shaking. Thus even after intensive shaking of the DNA-AuNP precipitate a purple solution with an UV/VIS maximum of 564 nm (Au8•Au9) is obtained.

4.4 Melting Experiments with Hybridized DNA-AuNP Conjugates

Melting experiments were performed with the assemblies formed by DNA-AuNP conjugates carrying complementary oligonucleotides. For this the aggregated DNA-AuNP conjugate solutions were heated (15° C.→75° C.) and the VIS absorption change at 520 nm was observed while stirring the DNA-AuNP solution. The $T_m$ values were determined by taking the maximum of the first derivative of a melting transition and are listed in Table 6.

Figure 5:
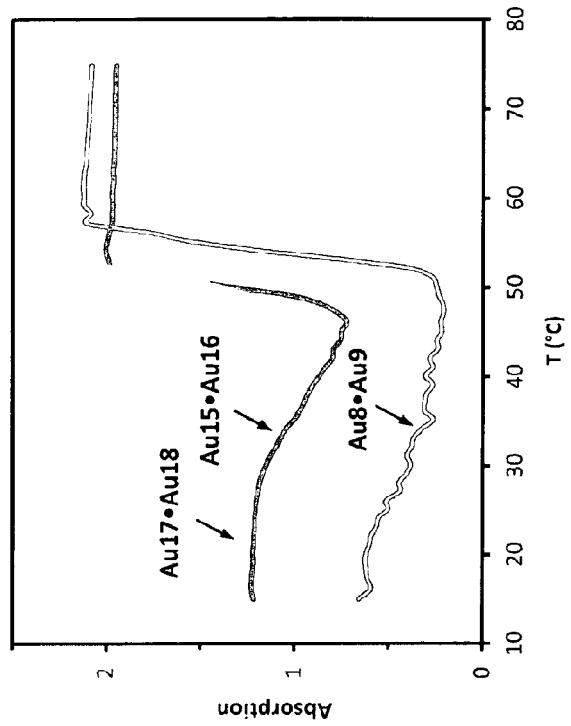
FIG. 5a is a melting profile of the free oligonucleotide duplex 8.9 observed at 260 nm and melting profiles of the assemblies Au8•Au9 and Au24•Au25, respectively, recorded at 520 nm.
FIG. 5b is the melting profiles of the assemblies Au8•Au9, Au15•Au16 and Au17•Au18), respectively, all recorded at 520 nm.
Figure 5:
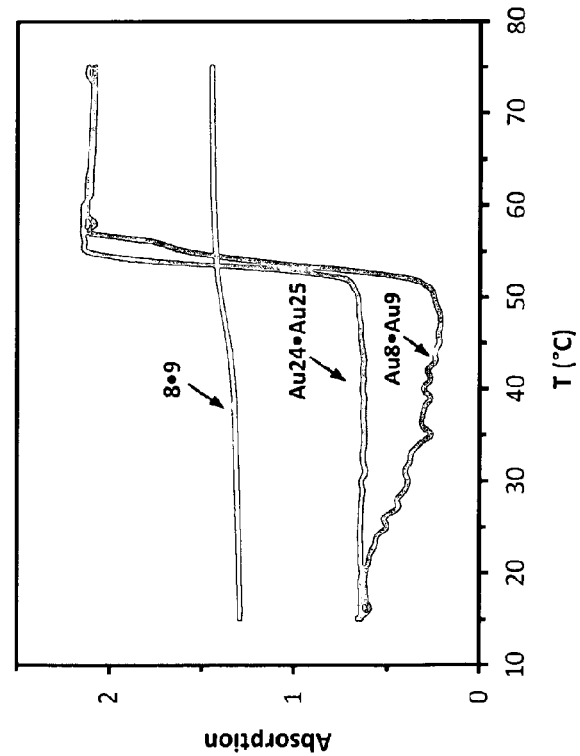
Figure 6:
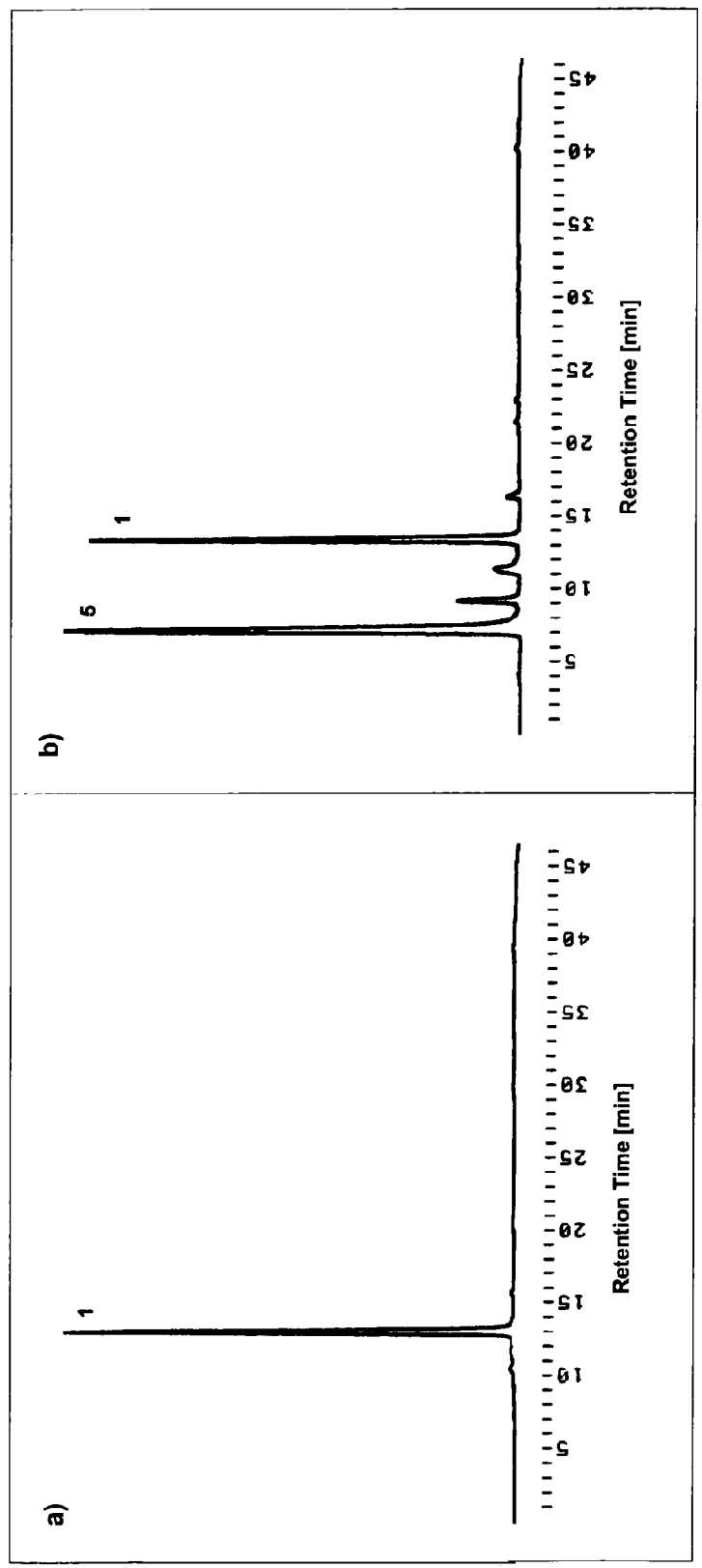
FIG. 6a is a reversed phase HPLC chromatogram relating to hydrolysis stability of 4-thio-2'-deoxythmidine (Compound 26; denoted in this Figure as 1), showing HPLC profile of 4-thio-2'-deoxythmidine (1). The compounds were analyzed by reversed-phase HPLC at 260 nm on a RP-18 column (250×4 mm). Gradient: 0-15 min 0-30% B in A, 30-40 min 30-40% B in A, 40-45 min 40-0% B in A, flow rate 0.7 cm$^3$ min$^{-1}$. 5 in this Figure is 5-Methyl-2'-deoxycytidine; verified by co-injection HPLC experiments.
FIG. 6b is a reversed phase HPLC chromatogram relating to hydrolysis stability of 4-thio-2'-deoxythmidine (Compound 26; denoted in this Figure as 1), showing HPLC profile obtained after treatment of 1 with 25% aq. ammonia at 60° C. for 16 h. The compounds were analyzed by reversed-phase HPLC at 260 nm on a RP-18 column (250×4 mm). Gradient: 0-15 min 0-30% B in A, 30-40 min 30-40% B in A, 40-45 min 40-0% B in A, flow rate 0.7 cm$^3$ min$^{-1}$. 5 in this Figure is 5-Methyl-2'-deoxycytidine; verified by co-injection HPLC experiments.
Figure 7:
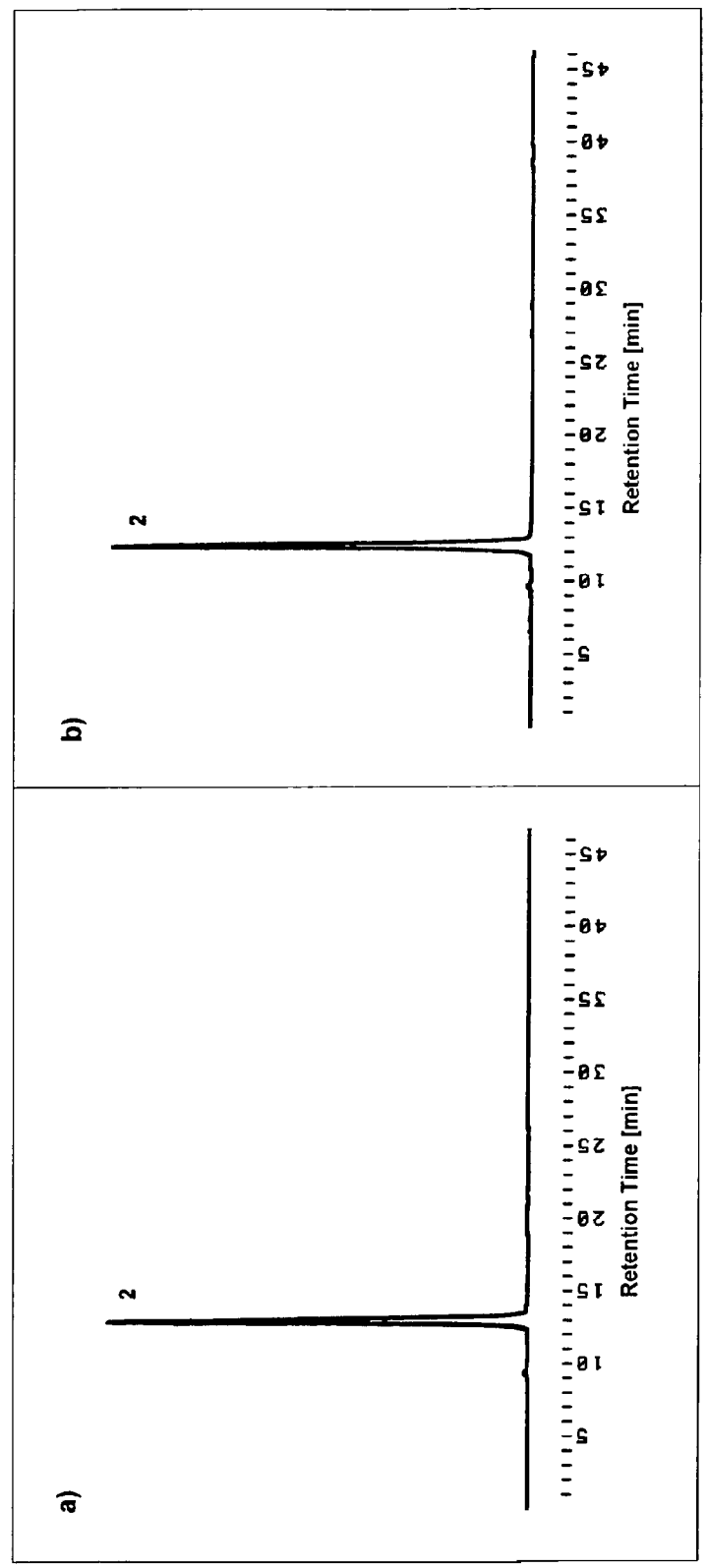
FIG. 7a is a reversed phase HPLC chromatogram relating to hydrolysis stability of 2-thio-2'-deoxythmidine (Compound 27; denoted in this Figure as 2) showing HPLC profile of 2-thio-2'-deoxythymidine (2). The compounds were analyzed by reversed-phase HPLC at 260 nm on a RP-18 column (250×4 mm). Gradient: 0-15 min 0-30% B in A, 30-40 min 30-40% B in A, 40-45 min 40-0% B in A, flow rate 0.7 cm$^3$ min$^{-1}$.
FIG. 7b is a reversed phase HPLC chromatogram profile relating to hydrolysis stability of 2-thio-2'-deoxythmidine (Compound 27; denoted in this Figure as 2) obtained after treatment of 2 with 25% aq. ammonia at 60° C. for 16 h. The compounds were analyzed by reversed-phase HPLC at 260 nm on a RP-18 column (250×4 mm). Gradient: 0-15 min 0-30% B in A, 30-40 min 30-40% B in A, 40-45 min 40-0% B in A, flow rate 0.7 cm$^3$ min$^{-1}$.
Figure 8:
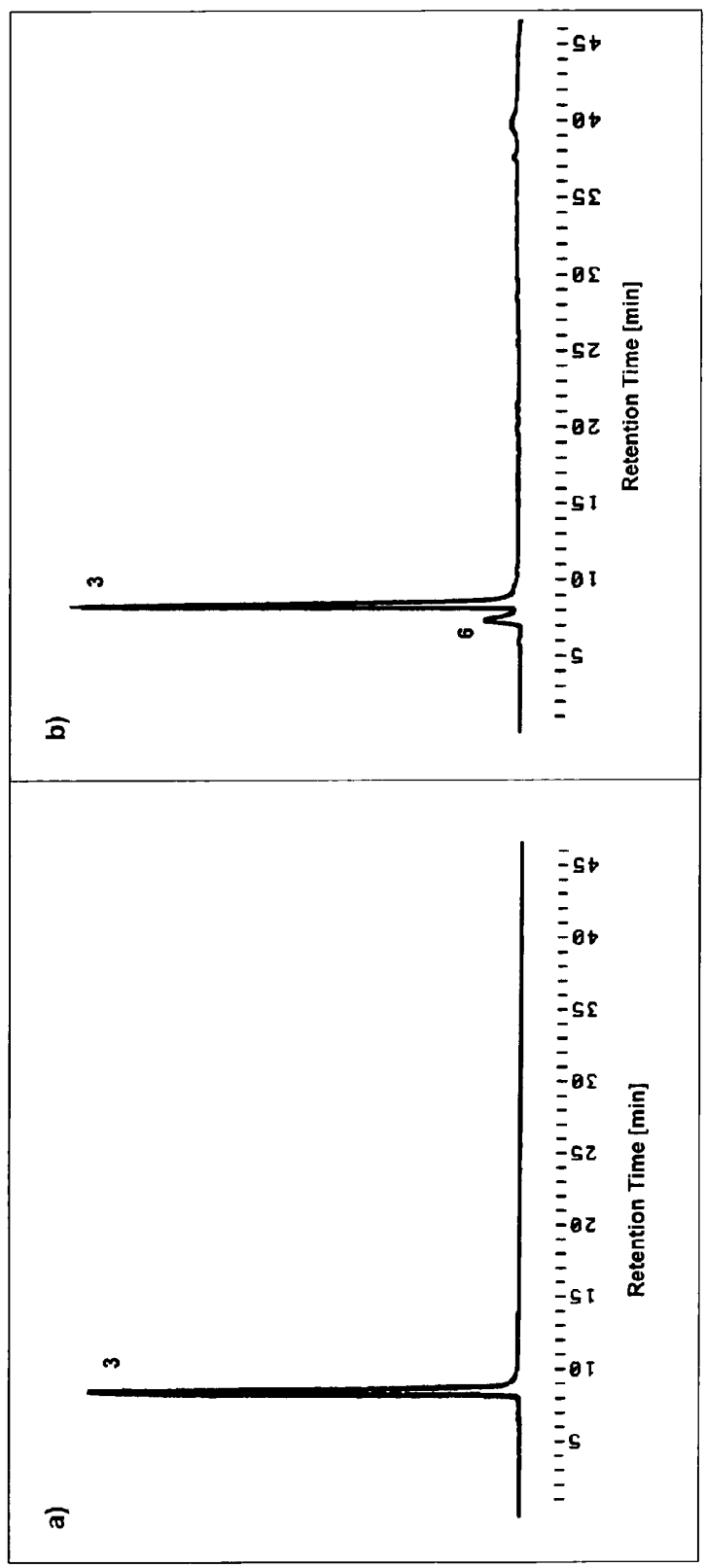
FIG. 8a is a reversed phase HPLC chromatogram relating to hydrolysis stability of 6-thio-2'-deoxyguanosine (Compound 28; denoted in this figure as 3) showing a HPLC profile of 6-thio-2'-deoxyguanosine (3). The compounds were analyzed by reversed-phase HPLC at 260 nm on a RP-18 column (250×4 mm). Gradient: 0-15 min 0-30% B in A, 30-40 min 30-40% B in A, 40-45 min 40-0% B in A, flow rate 0.7 cm$^3$ min$^{-1}$. 6 in this Figure is 2,6-Diaminopurine 2'-deoxyribonucleoside; verified by co-injection HPLC experiments.
FIG. 8b is a reversed phase HPLC chromatogram profile relating to hydrolysis stability of 6-thio-2'-deoxyguanosine (Compound 28; denoted in this figure as 3) obtained after treatment of 3 with 25% aq. ammonia at 60° C. for 16 h. The compounds were analyzed by reversed-phase HPLC at 260 nm on a RP-18 column (250×4 mm). Gradient: 0-15 min 0-30% B in A, 30-40 min 30-40% B in A, 40-45 min 40-0% B in A, flow rate 0.7 cm$^3$ min$^{-1}$. 6 in this Figure is 2,6-Diaminopurine 2'-deoxyribonucleoside; verified by co-injection HPLC experiments.
Figure 9:
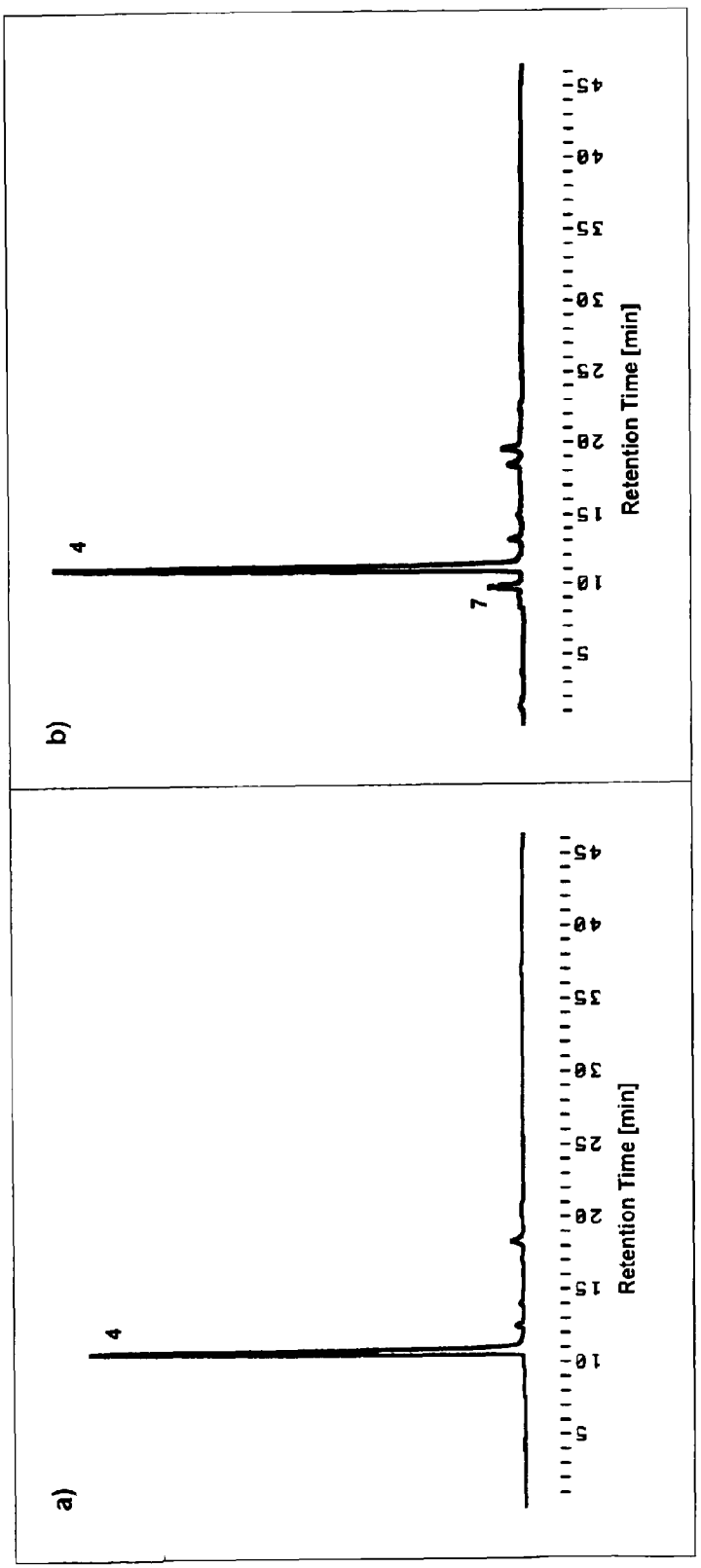
FIG. 9a is a reversed phase HPLC chromatogram of the hydrolysis stability of 7-deaza-6-thio-2'-deoxyguanosine (Compound 1; denoted in this figure as 4) showing HPLC profile of 7-deaza-6-thio-2'-deoxyguanosine (4). The compounds were analyzed by reversed-phase HPLC at 260 nm on a RP-18 column (250×4 mm). Gradient: 0-15 min 0-30% B in A, 30-40 min 30-40% B in A, 40-45 min 40-0% B in A, flow rate 0.7 cm$^3$ min$^{-1}$. 7 in this Figure is 2,6-Diamino-7-deazapurine 2'-deoxyribonucleoside; verified by co-injection HPLC experiments.
FIG. 9b is a reversed phase HPLC chromatogram profile of the hydrolysis stability of 7-deaza-6-thio-2'-deoxyguanosine (Compound 1; denoted in this figure as 4) obtained after treatment of 4 with 25% aq. ammonia at 60° C. for 16 h. The compounds were analyzed by reversed-phase HPLC at 260 nm on a RP-18 column (250×4 mm). Gradient: 0-15 min 0-30% B in A, 30-40 min 30-40% B in A, 40-45 min 40-0% B in A, flow rate 0.7 cm$^3$ min$^{-1}$. 7 in this Figure is 2,6-Diamino-7-deazapurine 2'-deoxyribonucleoside; verified by co-injection HPLC experiments.

A typical sharp melting profile of Au8•Au9 is shown in FIG. 5a indicating a $T_m$ value of 54° C. for the 3-dimensional interlinked network of Au nanoparticles assembled by duplex 8•9. For comparison, the dissociation of the network formed by conjugates Au24 and Au25 employing complementary oligonucleotides with thiolhexyl linker were investigated under exactly the same conditions as described for the Au8•Au9 assembly. For Au24•Au25 a $T_m$ value of 53° C. was determined (Table 6).

Both assemblies, employing a thiolhexyl linker (Au24•Au25) or thionucleside 1 (Au8•Au9), melting profiles with a very narrow melting transition (about 4° C. range) were detected as demonstrated in FIG. 5a whereas for the free oligonucleotide duplex 8•9 melting occurs over a much broader temperature range (about 20° C.) (FIG. 5a). This finding is consistent with observations made earlier by others reporting that oligonucleotides covalently bound to gold nanoparticles show highly cooperative melting properties of the networking duplex, which is reflected by a sharpened melting transition (Jin, R. et al., J. Am. Chem. Soc. 125 (2003) 1643-1654; Taton, T. A. et al., Science 289 (2000) 1757-1760).

TABLE 6

$T_m$ values of DNA-AuNP assemblies[a,b,c].

| DNA AuNP conjugates | $T_m$ [° C.] |
|---|---|
| 5'-d(S—(CH$_2$)$_6$ T$_{10}$ TAG GTC AAT ACT) (Au24)  (SEQ ID NO. 19)<br>3'-d(ATC CAG TTA TGA T$_{10}$-(CH$_2$)$_6$—S)(Au$_{25}$) (SEQ ID NO. 20) | 53 |
| 5'-d(1 T$_{10}$ TAG GTC AAT ACT)(Au8)  (SEQ ID NO. 5)<br>3'-d(ATC CAG TTA TGA T$_{10}$ 1)(Au9) (SEQ ID NO. 6) | 54 |
| 5'-d(11 T$_{10}$ TAG GTC AAT ACT)(Au15)  (SEQ ID NO. 10)<br>3'-d(ATC CAG TTA TGA T$_{10}$ 11)(Au16) (SEQ ID NO. 11) | 50 |

TABLE 6-continued $T_m$ values of DNA-AuNP assemblies[a,b,c].

| DNA AuNP conjugates | $T_m$ [° C.] |
|---|---|
| 5'-d(111 T₁₀ TAG GTC AAT ACT)(Au17)  (SEQ ID NO. 12)<br>3'-d(ATC CAG TTA TGA T₁₀ 111)(Au18) (SEQ ID NO. 13) | 51 |
| 5'-d(TA1 GTC AAT ACT TAG GTC AAT ACT)(Au21)  (SEQ ID NO. 16)<br>3'-d(ATC CAG TTA TGA ATC CAG TTA T1A)(Au22) (SEQ ID NO. 17) | 53 |
| 5'-d(TAG GTC AAT ACT TA1 GTC AAT ACT)(Au23) (SEQ ID NO. 18)<br>3'-d(ATC CAG TTA T1A ATC CAG TTA TGA)(Au6)  (SEQ ID NO. 1) | n.m. |

[a]Measured at 520 nm in 0.1 M NaCl, 10 mM phosphate buffer (pH 7.0) with $A_{520}$ = 2.1 for each DNA-AuNP conjugate solution.

[b] = 15 nm diameter gold nanoparticle.

[c]Spacer $T_{10}$ = TTT TTT TTT T.

n.m. no melting observed.

Moreover, AuNPs functionalized with multiple 5'-overhanging thionucleosides 1 were allowed to hybridize DNA-AuNP conjugates carrying the complementary oligonucleotide (→Au15•Au16, Au17•Au18). As shown in Table 6, these conjugate assemblies exhibit very similar $T_m$ values (Au15•Au16: $T_m$=50° C.; Au17•Au18: $T_m$=51° C.). Compared to the $T_m$ value found for the assembly Au8•Au9 employing only one thionucleoside (1) per oligonucleotide strand, these values are 3-4° C. lower but still in the same range. The melting profiles of Au8•Au9, Au15•Au16 and Au17•Au18 indicating the narrow melting transition range (around 4° C.) are shown in FIG. 5b.

The melting behaviour of the DNA-AuNP assemblies carrying 24-mer oligonucleotides which use thionucleosides 1 as anchor molecule at different internal position within their sequence was also investigated (Au21•Au22, Au23•Au6). These oligonucleotides are composed of a 2-fold repeated recognition sequence allowing formation of 24 base pairs or partial hybridization (12 base pairs). A $T_m$ value of 53° C. was detected for the assembly Au21•Au22 with thionucleoside 1 being located at the periphery of the 24-mer oligonucleotide sequences. This $T_m$ value points to a partial hybridization of the oligonucleotides within the DNA-AuNP assembly, such as (i) a fully matched duplex with fraying ends and base pairing only in the centre of the duplex or (ii) partial hybridization of the duplex leaving the unpaired nucleosides as spacers between the recognition site and the gold nanoparticle as shown in Table 6, entry 5.

Contrary, the closely related DNA-AuNP conjugates Au23 and Au6 also employing complementary oligonucleotides but with compound 1 located in the centre of each oligonucleotide cannot form a DNA-AuNP interlinked network. Even incubation overnight did not lead to a colour change of the combined conjugate solution and no shifting of the VIS maximum was observed. Thus, no aggregation occurred. This result demonstrates that a distance between recognition site and gold nanoparticle is necessary for assembly formation.

Example 5

Stability of Various Thiooxonucleoside Under Deprotection Conditions

The stability of the thiooxo group of several nucleosides (1, 26-28) was tested in alkaline solution (standard oligonucleotide deprotection conditions: 25% aqueous $NH_3$, 14-16 h, 60° C.).

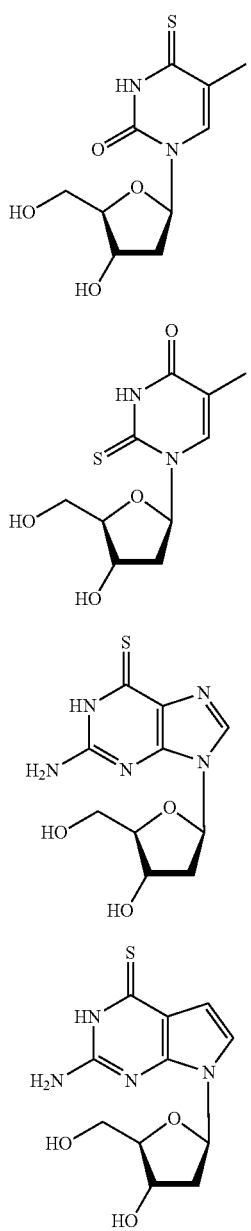

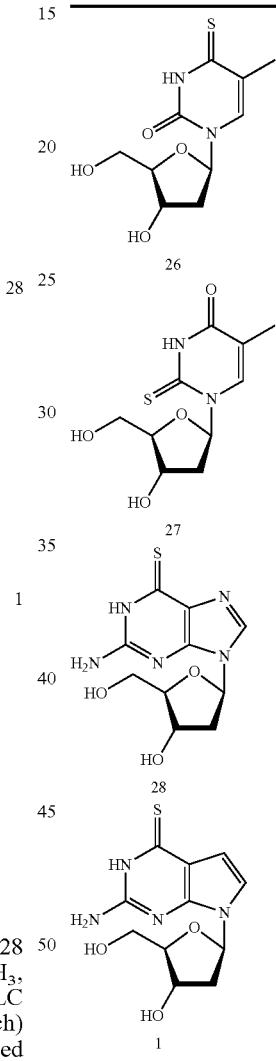

The hydrolysis stability of thiooxonucleosides 1, 26-28 under standard deprotection conditions (25% aqueous $NH_3$, 14-16 h, 60° C.) was monitored by reversed-phase HPLC (RP-18, 250×4 mm). Nucleosides 1, 26-28 (about 1 mg each) were dissolved in 1 ml 25% aq. ammonia soln. in a sealed vessel and incubated at 60° C. After 16 h incubation, aq. ammonia was removed by evaporation and the residue was redissolved in 1 ml HPLC buffer A. 50 μl of each sample was injected into the HPLC apparatus and spectra were recorded at 260 nm. The following solvent gradient system was used: [A: 0.1 M $(Et_3NH)OAc$ (pH 7.0)/MeCN 95:5; B: MeCN; gradient: 0-15 min 0-30% B in A, 30-40 min 30-40% B in A, 40-45 min 40-0% B in A, flow rate 0.7 $cm^3$ $min^{-1}$]. Quantification of the constituents was made on the basis of the peak areas, which were divided by the extinction coefficients of nucleosides ($\epsilon_{260}$) in HPLC buffer A.

The following extinction coefficients of nucleosides ($\epsilon_{260}$) were used: 26 (1500), 27 (6300), 28 (7300), and 1 (10100).

As obvious from Table 7, as well as from the corresponding FIGS. 6 to 9, nucleosides 27, 28 and 1 show a decent stability whereas nucleoside 26 was found to be rather unstable.

TABLE 7

Conversion of thiooxonucleosides 1, 26 -28 after incubation in aq. ammonia for 16 h at 60° C.

| Nucleoside | Conversion in % |
|---|---|
| 26 | 32.1 |
| 27 | <1% |
| 28 | 8.6 |
| 1 | 7.3 |

Example 6

Conjugation of Various Oligonucleotides Incorporating Different Thiooxonucleosides to Gold Nanoparticles 6.1 Synthesis, Purification and Characterization of Oligonucleotides.

Figure 10:
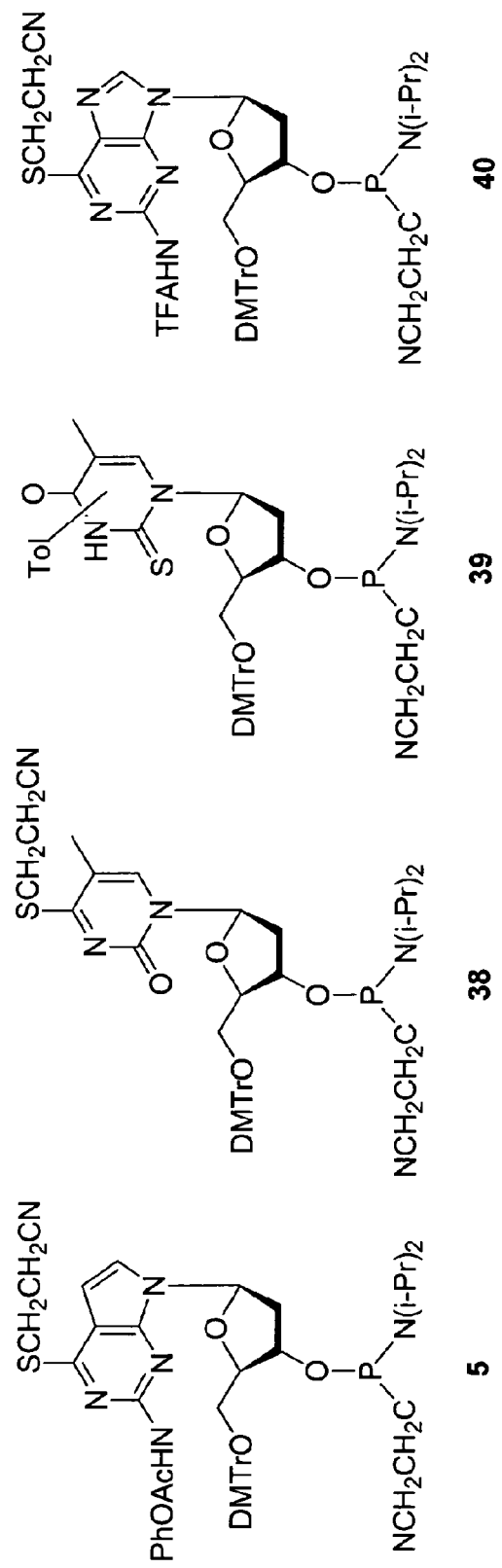
FIG. 10 presents the different phosphoroamidites building blocks for several different thiooxonucleotides employed in oligonucleotide synthesis.

A series of oligonucleotides (8-9, 32-37) containing nucleosides 1, 26-28 (see Table 8) were synthesized on solid phase at 1 μm scale using the regular phosphoroamidites and the phosphoroamidites 5, 38-40 (see FIG. 10) following the protocol for 3'-(2-cyanoethyl)-phosphoroamidite chemistry. After cleavage from the solid support, oligonucleotides containing 27 or 1 were deprotected in 25% aqueous $NH_3$ solution for 14-16 h at 60° C. (standard deprotection conditions). Oligonucleotides incorporating 26 or 28 were deprotected in 25% aqueous $NH_3$ solution containing 50 mM NaSH overnight at room temperature (recommended conditions of the supplier). The DMT-containing oligonucleotides were purified on reversed-phase HPLC in the DMT-on modus (Merck-Hitachi-HPLC; RP-18 column) with the following gradient system [A: 0.1 M $(Et_3NH)OAc$ (pH 7.0)/MeCN 95:5; B: MeCN]: 3 min, 20% B in A, 12 min, 20-50% B in A and 25 min, 20% B in A, flow rate 1.0 ml/min. The solvent was evaporated and the oligonucleotides were treated with 2.5% $Cl_2CHCOOH/CH_2Cl_2$ (400 µl) for 5 min at 0° C. to remove the 4,4'-dimethoxytrityl residues. The detritylated oligomers were purified again by reversed-phase HPLC [gradient: 0-20 min 0-20% B in A; flow rate 1 ml/min]. The oligomers were desalted on a short column (RP-18, silica gel) using $H_2O$ for elution of the salt, while the oligomers were eluted with $MeOH/H_2O$ (3:2). The oligonucleotides were lyophilized on a Speed-Vac evaporator to yield colorless solids which were frozen at −24° C.

The molecular masses of the oligonucleotides 8-9, 32-37 were determined by MALDI-TOF mass spectrometry in the linear negative mode. The detected masses were identical with the calculated values (Table 8).

TABLE 8

Single-stranded oligonucleotides used for conjugation to AuNPs.

| Oligonucleotides | MW (calcd) | MW (found) |
|---|---|---|
| 5'-d(26-$T_{10}$-TAG GTC AAT ACT) (32) (SEQ ID NO. 21) | 7006.68 | 7007.16 |
| 5'-d(26-$T_{10}$-AGT ATT GAC CTA) (33) (SEQ ID NO. 22) | 7006.68 | 7006.38 |
| 5'-d(27-$T_{10}$-TAG GTC AAT ACT) (34) (SEQ ID NO. 23) | 7006.68 | 7006.71 |
| 5'-d(27-$T_{10}$-AGT ATT GAC CTA) (35) (SEQ ID NO. 24) | 7006.68 | 7007.20 |
| 5'-d(28-$T_{10}$-TAG GTC AAT ACT) (36) (SEQ ID NO. 25) | 7031.69 | 7032.49 |

TABLE 8-continued

Single-stranded oligonucleotides used for conjugation to AuNPs.

| Oligonucleotides | MW (calcd) | MW (found) |
|---|---|---|
| 5'-d(28-$T_{10}$-AGT ATT GAC CTA) (37) (SEQ ID NO. 26) | 7031.69 | 7032.96 |
| 5'-d(1-$T_{10}$-TAG GTC AAT ACT) (8) (SEQ ID NO. 5) | 7030.17 | 7030.81 |
| 5'-d(1-$T_{10}$-AGT ATT GAC CTA) (9) (SEQ ID NO. 6) | 7030.17 | 7031.08 |

Spacer $T_{10}$ = 5'-d(TTT TTT TTT T).

6.2 General Procedure for the Preparation of Oligonucleotide Gold Nanoparticle Conjugates Employing Thiooxonucleosides as Molecular Anchor.

A 15 nm gold nanoparticle solution was prepared from a $HAuCl_4$ solution by citrate reduction according to the protocol reported by Turkevich and later described by Letsinger and Mirkin (Mirkin, C. A. et al., Nature 283 (1996) 607-609; Elghanian, R., et al., Science 277 (1997) 1078-1081; Turkevich, J. et al., Faraday Soc. 11 (1951) 55-75). The gold nanoparticles (~3 nM) were functionalized with oligonucleotides 8-9, 32-37 containing one of the thiooxonucleosides 1, 26-28 at their 5'-ends (Table 2). The DNA-AuNPs conjugates were prepared by mixing 1 ml of the gold nanoparticle solution with the purified oligonucleotide solution (final oligonucleotide concentration of 3 µM). The coupling reaction was performed at slightly elevated temperature (40° C.). After standing for 20 h, 5 µl of a 2 M NaCl, 0.2 mM phosphate buffer solution (pH 7.0) were added under constant stirring to increase the NaCl concentration of the nanoparticle solution to 0.01 M. The solutions were incubated for 6-8 h at 40° C. This procedure was repeated three times to increase the NaCl concentration of the nanoparticle conjugate solution stepwise from 0.02 M, 0.05 M and finally to 0.1 M NaCl. In between the solutions were always allowed to age for 6-8 h at 40° C. Subsequently, the DNA gold nanoparticle solutions were centrifuged (8000 rpm) and the clear supernatant was taken off to remove unbound oligonucleotides. The precipitate was redispersed in 1 ml of a 0.1 M NaCl, 10 mM phosphate buffer solution (pH 7.0). After incubation (24 h, 40° C.), the nanoparticle solutions were washed again with the same buffer (0.1 M NaCl, 10 mM phosphate buffer, pH 7.0), finally yielding 1 ml of the DNA-AuNPs conjugates Au8-Au9, Au32-Au37.

TABLE 9

Applicability of thiooxonucleosides 1, 26-28 for gold nanoparticle conjugate formation.

| Entry | Nucleoside | Conjugate 5'-d(X $T_{10}$ TAG GTC AAT ACT) | Conjugate 5'-d(X $T_{10}$ AGT ATT GAC CTA) | Hybridization of complementary conjugates[c] |
|---|---|---|---|---|
| 1 | X = 26 | Au32: yes[a]/no[b] (SEQ ID NO. 21) | Au33: yes[a]/no[b] (SEQ ID NO. 22) | yes |
| 2 | X = 27 | Au34: yes[a]/no[b] (SEQ ID NO. 23) | Au35: yes[a]/no[b] (SEQ ID NO. 24) | no |
| 3 | X = 28 | Au36: yes[a,b] (SEQ ID NO. 25) | Au37: yes[a,b] (SEQ ID NO. 26) | yes* |

TABLE 9-continued

Applicability of thiooxonucleosides 1, 26-28 for gold nanoparticle conjugate formation.

| Entry | Nucleoside | Conjugate 5'-d(X T$_{10}$ TAG GTC AAT ACT) | Conjugate 5'-d(X T$_{10}$ AGT ATT GAC CTA) | Hybridization of complementary conjugates[c] |
|---|---|---|---|---|
| 4 | X = 1 | Au8: yes[a,b] (SEQ ID NO. 5) | Au9: yes[a,b] (SEQ ID NO. 6) | yes |

[structures of compounds 26, 27, 28, and 1 shown]

[a]Stable oligonucleotide gold nanoparticle conjugates were obtained in 0.1 M NaCl, 10 mM phosphate buffer, pH 7.0.
[b]Stable oligonucleotide gold nanoparticle conjugates were obtained in 0.2 M NaCl, 10 mM phosphate buffer, pH 7.0.
[c]The hybridization experiment was performed in 0.1 M NaCl, 10 mM phosphate buffer, pH 7.0 with overnight incubation time.
*Formation of the DNA gold nanoparticle network occurred much slower and required several days.
Spacer T$_{10}$ = 5'-d(TTT TTT TTT T).

 = 15 nm diameter gold nanoparticle.

6.2.1 Experimental Details for 4-Thio-2'-Deoxythmidine

The UV-VIS spectra of the oligonucleotides 32 and 33 containing 4-thio-2'-deoxythymidine (26) show the characteristic UV absorption at 337 nm due to the thiooxo group of nucleoside 26 (reported literature value for 26: 335 nm; Fox, J. J. et al., J. Am. Chem. Soc. 81 (1959) 178-187) (FIG. 9a). DNA-AuNPs employing oligonucleotide 32 or 33 were prepared as described above. The resulting DNA-AuNP conjugates Au32 and Au33 show plasmon resonance at 524 nm indicating a non-aggregated state. The stability of DNA-AuNP conjugates Au32 and Au33 was further tested in a 0.2 M NaCl, 10 mM phosphate, pH 7 buffer solution. After incubation overnight in the presence of 0.2 M NaCl in a glass cuvette, both conjugates show plasmon resonance at 524.5 nm. However, it was found that a significant amount of the DNA-AuNP conjugates adheres at the glass surface of the cuvette. Due to this, the height of absorbance of the DNA-AuNP conjugate solution decreased by about 36% from the original value. Based on this result, DNA-AuNP conjugates using 4-thio-2'-deoxythymidine (26) as anchor molecule are classified as not stable in the presence of 0.2 M NaCl (see Table 9, entry 1).

Next, the hybridization properties of the oligonucleotide AuNP conjugates incorporating thionucleoside 26 were investigated. In a typical experiment, 0.5 ml of a 0.1 M NaCl, 10 mM phosphate, pH 7 buffer solution containing DNA-AuNP conjugate Au32 and 0.5 ml of a 0.1 M NaCl, 10 mM phosphate, pH 7 buffer solution containing DNA-AuNP conjugate Au33 were mixed together (equal concentrations). The solution containing DNA-AuNP conjugates Au32 and Au33 was allowed to incubate overnight. During this, slow hybridization of the complementary oligonucleotide AuNP conjugates Au32 and Au33 occurred evidenced by slow red shifting (524 nm→548 nm) and broadening of the plasmon resonance band concomitant by a red to purple colour change. Finally, precipitation of the DNA gold nanoparticle network was observed resulting in a clear supernatant and a dark precipitate. After intensive shaking of the DNA-AuNP solution, the precipitate can be re-dispersed leading to a purple solution with an UV/VIS maximum of 548 nm.

6.2.2 Experimental Details for 2-Thio-2'-Deoxythmidine

The UV spectra of the oligonucleotides 34 and 35 show only one absorption maximum at 264 nm (reported literature value for 27: 264 nm; Vorbrueggen, H. et al., Chem. Ber. 106 (1973) 3039-3061). DNA-AuNPs employing oligonucleotide 34 or 35 were prepared as described above. The resulting DNA-AuNP conjugates Au-16 and Au-17 show plasmon resonance at 524 nm indicating a non-aggregated state in a 0.1 M NaCl, 10 mM phosphate, pH 7 buffer solution. However, in the presence of 0.2 M NaCl (10 mM phosphate, pH 7 buffer) aggregation (solution turns black) followed by precipitation occurred immediately. Based on this result, DNA-AuNP conjugates using 2-thio-2'-deoxythymidine (27) as anchor molecule are classified as not stable in the presence of 0.2 M NaCl (see Table 9, entry 2).

Next, hybridization of the oligonucleotide AuNP conjugates incorporating thionucleoside 27 was tested. In a typical experiment, 0.5 ml of a 0.1 M NaCl, 10 mM phosphate, pH 7 buffer solution containing DNA-AuNP conjugate Au34 and 0.5 ml of a 0.1 M NaCl, 10 mM phosphate, pH 7 buffer solution containing DNA-AuNP conjugate Au35 were mixed together (equal concentrations). The solution containing DNA-AuNP conjugates Au34 and Au35 was allowed to incubate overnight. No colour change of the DNA-AuNP conjugate solution was observed. The UV/VIS spectrum of the DNA-AuNP solution containing the complementary conjugates Au34 and Au35 showed plasmon resonance at 524 nm indicating a non-aggregated state.

6.2.3 Experimental Details for 6-Thio-2'-Deoxyguanosine

The UV-VIS spectra of the oligonucleotides 36 and 37 containing 6-thio-2'-deoxyguanosine (28) show the characteristic UV absorption at 343 nm due to the thioxo group of nucleoside 28 (reported literature value for 28: 341 nm; Iwamoto, R. H. et al., J. Med. Chem. 6 (1963) 684-688). DNA-AuNPs employing oligonucleotide 36 or 37 were prepared following the procedure described above. However, we found that the preparation of DNA-AuNP conjugates with 36 or 37 was encountered with difficulties. Conjugation of the oligonucleotides 36 and 37 to the AuNP failed several times (50% failure). Also, the centrifugation speed had to be reduced significantly from 8000 rpm (standard speed) to 5800 rpm, otherwise it was not possible to redisperse the precipitate.

The obtained DNA-AuNP conjugates Au36 and Au37 show plasmon resonance at 524 nm indicating a non-aggregated state. The stability of DNA-AuNP conjugates Au36 and Au37 was further tested in a 0.2 M NaCl, 10 mM phosphate, pH 7 buffer solution (FIG. 13). After incubation overnight in the presence of 0.2 M NaCl in a glass cuvette, both conjugates show plasmon resonance at 525 nm. Only a small amount of the DNA-AuNP conjugates adheres at the glass surface of the cuvette. The height of absorbance of the DNA-AuNP conjugate solution decreased by 10-14% from the original value (FIG. 13). Based on this result, DNA-AuNP conjugates using 6-thio-2'-deoxyguanosine (28) as anchor molecule are classified as stable in the presence of 0.2 M NaCl (see Table 9, entry 3).

Next, the hybridization properties of the oligonucleotide AuNP conjugates incorporating thionucleoside 28 were investigated. In a typical experiment, 0.5 ml of a 0.1 M NaCl, 10 mM phosphate, pH 7 buffer solution containing DNA-AuNP conjugate Au36 and 0.5 ml of a 0.1 M NaCl, 10 mM phosphate, pH 7 buffer solution containing DNA-AuNP conjugate Au37 were mixed together (equal concentrations). The solution containing DNA-AuNP conjugates Au36 and Au37 was allowed to incubate overnight. Only a slight colour change of the DNA-AuNP conjugate solution was observed. The UV/VIS spectrum of the DNA-AuNP solution containing the complementary conjugates Au36 and Au37 shows a red shifting (524 nm→538 nm) of the plasmon resonance band, decrease of the absorption and a slight broadening of the plasmon resonance band. But we did not observe precipitation of the DNA-AuNPs as described for 4-thio-2'-deoxythymidine (26) or 7-deaza-6-thio-2'-deoxyguanosine (1) after one night of incubation (see section 6.2.1 and 6.2.4). Only after several days (about 1 week), precipitation of the DNA gold nanoparticle network was observed resulting in a clear supernatant and a dark precipitate. After intensive shaking of the DNA-AuNP solution, the precipitate can be re-dispersed leading to a purple solution with an UV/VIS maximum of 549.5 nm.

6.2.4 Experimental Details for 7-Deaza-6-Thio-2'-Deoxyguanosine

The UV-VIS spectra of the oligonucleotides 8 and 9 containing 7-deaza-6-thio-2'-deoxyguanosine (1) show the characteristic UV absorption at 345 nm due to the thiooxo group of nucleoside 1 (reported literature values for 1: 345 nm; Seela, F. et al., Liebigs Ann. Chem. 1 (1987) 15). DNA-AuNPs employing oligonucleotide 8 or 9 were prepared as described above. The resulting DNA-AuNP conjugates Au8 and Au9 show plasmon resonance at 524 nm indicating a non-aggregated state. The DNA-AuNP conjugates Au8 and Au9 were also redispersed in a 0.2 M NaCl, 10 mM phosphate, pH 7 buffer solution.

After incubation overnight in the presence of 0.2 M NaCl in a glass cuvette, both conjugates show plasmon resonance at 524.5 nm. Only a small amount of the DNA-AuNP conjugates adheres at the glass surface of the cuvette. The height of absorbance of the DNA-AuNP conjugate solution decreased by 10-14% from the original value. Based on this result, DNA-AuNP conjugates using 7-deaza-6-thio-2'-deoxyguanosine (1) as anchor molecule are classified as stable in the presence of 0.2 M NaCl (see Table 9, entry 4).

Next, the hybridization properties of the oligonucleotide AuNP conjugates incorporating thionucleoside 1 were investigated. In a typical experiment, 0.5 ml of a 0.1 M NaCl, 10 mM phosphate, pH 7 buffer solution containing DNA-AuNP conjugate Au8 and 0.5 ml of a 0.1 M NaCl, 10 mM phosphate, pH 7 buffer solution containing DNA-AuNP conjugate Au9 were mixed together (equal concentrations). The solution containing DNA-AuNP conjugates Au8 and Au9 was allowed to incubate overnight. During this, slow hybridization of the complementary oligonucleotide AuNP conjugates Au8 and Au9 occurred evidenced by slow red shifting (524 nm→567 nm) and broadening of the plasmon resonance band concomitant by a red to purple colour change. Finally, precipitation of the DNA gold nanoparticle network was observed resulting in a clear supernatant and a dark precipitate. After intensive shaking of the DNA-AuNP solution, the precipitate can be re-dispersed leading to a purple solution with an UV/VIS maximum of 567 nm.

From the experiments summarized above, see especially Table 9, it would appear that an oligonucleotide-gold conjugate, wherein the oligonucleotide comprises a thiooxonucleotide based on a nucleoside according to Formula I (e.g. substances 1 and 28 of Table 9), is at least in certain technical aspects superior to an oligonucleotide-gold conjugate, wherein the oligonucleotide comprises a thiooxonucleotide as known from prior art (e.g. substances 26 and 27, respectively, of Table 9).

All references cited in this specification are herewith incorporated by reference with respect to their entire disclosure content and the disclosure content specifically mentioned in this specification.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within the known or customary practice in the art to which this disclosure pertains.

What is claimed is:

1. An oligonucleotide-solid phase conjugate comprising:
a solid phase comprising a metal; and
an oligonucleotide comprising a thiooxonucleobase according to Formula I,

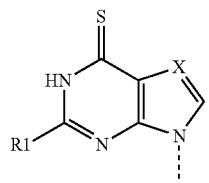

wherein X is CH or N, R1 is H or NH2, and --- indicates a covalent bond, said oligonucleotide being bound to said solid phase via a sulphur atom of said thiooxonucleotide.

2. The oligonucleotide-solid phase conjugate of claim 1, wherein X of Formula I is CH.

3. The oligonucleotide-solid phase conjugate of claim 1, wherein said solid phase comprises a thiophilic metal.

4. The oligonucleotide-solid phase conjugate of claim 3, wherein the thiophilic metal is selected from a group consisting of a thiophilic noble metal and a semiconductor nanocrystal comprising a thiophilic metal.

5. The oligonucleotide-solid phase conjugate according of claim 3, wherein the thiophilic metal is a noble metal selected from the group consisting of gold and silver.

6. The oligonucleotide-solid phase conjugate of claim 5, wherein the thiophilic metal is gold.

7. The oligonucleotide-solid phase conjugate of claim 1, wherein the solid phase is a gold nanoparticle.

8. The oligonucleotide-solid phase conjugate of claim 1, wherein the metal is gold present as a layer on a solid support.

9. The oligonucleotide-solid phase conjugate of claim 1, wherein the solid phase is a thiophilic semiconductive material.

10. The oligonucleotide-solid phase conjugate of claim 9, wherein the thiophilic semiconductive material is present as a nanocrystal.

11. The oligonucleotide-solid phase conjugate of claim 1, wherein the oligonucleotide is at least 8 nucleotides in length.

12. A method of producing an oligonucleotide-solid phase conjugate, the method comprising the steps of:
a) providing a solid phase comprising a metal; and
b) binding an oligonucleotide to said solid phase, said oligonucleotide containing a thiooxonucleobase according to Formula I,

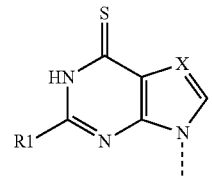

wherein X is CH or N, R1 is H or NH2, and --- indicates a covalent bond.

13. The method of claim 12, wherein the oligonucleotide comprises a thiooxonucleotide based on a nucleoside of Formula I being a 7-deazanucleotide, wherein X is CH.

14. The method of claim 12, wherein the oligonucleotide is at least 8 nucleotides in length.

15. The method of claim 12, wherein the solid phase comprises a thiophilic metal.

* * * * *

SEQUENCE LISTING

```
<160> NUMBER OF SEQ ID NOS: 27

<210> SEQ ID NO 1
<211> LENGTH: 24
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (14)..(14)
<223> OTHER INFORMATION: "h" indicates compound 1 (7-deaza-6-thio-2'-
      deoxyguanosine)

<400> SEQUENCE: 1
agtattgacc taahtattga ccta                                          24

<210> SEQ ID NO 2
<211> LENGTH: 12
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (7)..(7)
<223> OTHER INFORMATION: "h" indicates compound 1 (7-deaza-6-thio-2'-
      deoxyguanosine)

<400> SEQUENCE: 2
agtatthacc ta                                                       12

<210> SEQ ID NO 3
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(1)
<223> OTHER INFORMATION: "h" indicates compound 1 (7-deaza-6-thio-2'-
      deoxyguanosine)

<400> SEQUENCE: 3
``` htttttttttt ttaggtcaat act        23

<210> SEQ ID NO 4
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(1)
<223> OTHER INFORMATION: "h" indicates compound 1 (7-deaza-6-thio-2'-
      deoxyguanosine)

<400> SEQUENCE: 4 htttttttttt tagtattgac cta        23

<210> SEQ ID NO 5
<211> LENGTH: 12
<212> TYPE: DNA
<213> ORGANISM: Artificial Sequence
<220> FEATURE:
<223> OTHER INFORMATION: Oligonucleotide Sequence

<400> SEQUENCE: 5
taggtcaata ct        12

<210> SEQ ID NO 6
<211> LENGTH: 12
<212> TYPE: DNA
<213> ORGANISM: Artificial Sequence
<220> FEATURE:
<223> OTHER INFORMATION: Oligonucleotide Sequence

<400> SEQUENCE: 6
agtattgacc ta        12

<210> SEQ ID NO 7
<211> LENGTH: 12
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (2)..(2)
<223> OTHER INFORMATION: "h" indicates compound 1 (7-deaza-6-thio-2'-
      deoxyguanosine)

<400> SEQUENCE: 7
ahtattgacc ta        12

<210> SEQ ID NO 8
<211> LENGTH: 12
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (3)..(4)
<223> OTHER INFORMATION: "h" indicates compound 1 (7-deaza-6-thio-2'-
      deoxyguanosine)

<400> SEQUENCE: 8
tahhtcaata ct        12

<210> SEQ ID NO 9

```
<211> LENGTH: 12
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (2)..(2)
<223> OTHER INFORMATION: "h" indicates compound 1 (7-deaza-6-thio-2'-
      deoxyguanosine)
<220> FEATURE:
<221> NAME/KEY: modified_base
<222> LOCATION: (7)..(7)
<223> OTHER INFORMATION: "h" indicates compound 1 (7-deaza-6-thio-2'-
      deoxyguanosine)

<400> SEQUENCE: 9
ahtatthacc ta                                                        12

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(2)
<223> OTHER INFORMATION: "h" indicates compound 1 (7-deaza-6-thio-2'-
      deoxyguanosine)

<400> SEQUENCE: 10
hhtttttttt tttaggtcaa tact                                           24

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(2)
<223> OTHER INFORMATION: "h" indicates compound 1 (7-deaza-6-thio-2'-
      deoxyguanosine)

<400> SEQUENCE: 11
hhtttttttt ttagtattga ccta                                           24

<210> SEQ ID NO 12
<211> LENGTH: 25
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(3)
<223> OTHER INFORMATION: "h" indicates compound 1 (7-deaza-6-thio-2'-
      deoxyguanosine)

<400> SEQUENCE: 12 hhhtttttttt ttttaggtca atact                                         25

<210> SEQ ID NO 13
<211> LENGTH: 25
<212> TYPE: DNA
<213> ORGANISM: Artificial Sequence
<220> FEATURE:
<223> OTHER INFORMATION: Oligonucleotide Sequence
<220> FEATURE:
```

```
<221> NAME/KEY: modified_base
<222> LOCATION: (1)..(3)
<223> OTHER INFORMATION: "h" indicates compound 1 (7-deaza-6-thio-2'-
      deoxyguanosine)

<400> SEQUENCE: 13
hhhttttttt tttagtattg accta                                              25

<210> SEQ ID NO 14
<211> LENGTH: 24
<212> TYPE: DNA
<213> ORGANISM: Artificial Sequence
<220> FEATURE:
<223> OTHER INFORMATION: Oligonucleotide Sequence

<400> SEQUENCE: 14
taggtcaata cttaggtcaa tact                                               24

<210> SEQ ID NO 15
<211> LENGTH: 24
<212> TYPE: DNA
<213> ORGANISM: Artificial Sequence
<220> FEATURE:
<223> OTHER INFORMATION: Oligonucleotide Sequence

<400> SEQUENCE: 15
agtattgacc taagtattga ccta                                               24

<210> SEQ ID NO 16
<211> LENGTH: 24
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (3)..(3)
<223> OTHER INFORMATION: "h" indicates compound 1 (7-deaza-6-thio-2'-
      deoxyguanosine)

<400> SEQUENCE: 16
tahgtcaata cttaggtcaa tact                                               24

<210> SEQ ID NO 17
<211> LENGTH: 24
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (2)..(2)
<223> OTHER INFORMATION: "h" indicates compound 1 (7-deaza-6-thio-2'-
      deoxyguanosine)

<400> SEQUENCE: 17
ahtattgacc taagtattga ccta                                               24

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (15)..(15)
<223> OTHER INFORMATION: "h" indicates compound 1 (7-deaza-6-thio-2'-
      deoxyguanosine)
```

-continued

```
<400> SEQUENCE: 18
taggtcaata cttahgtcaa tact                                            24

<210> SEQ ID NO 19
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: misc_feature
<222> LOCATION: (1)..(1)
<223> OTHER INFORMATION: "h" indicates Trityl-S-(CH2

<400> SEQUENCE: 19 htttttttt ttaggtcaat act                                              23

<210> SEQ ID NO 20
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: misc_feature
<222> LOCATION: (1)..(1)
<223> OTHER INFORMATION: "h" indicates Trityl-S-(CH2)6

<400> SEQUENCE: 20 htttttttt tagtattgac cta                                              23

<210> SEQ ID NO 21
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(1)
<223> OTHER INFORMATION: "h" indicates compound 26 (4-thio-2'-
      deoxythymidine)

<400> SEQUENCE: 21 htttttttt ttaggtcaat act                                              23

<210> SEQ ID NO 22
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(1)
<223> OTHER INFORMATION: "h" indicates compound 26 (4-thio-2'-
      deoxythymidine)

<400> SEQUENCE: 22 htttttttt tagtattgac cta                                              23

<210> SEQ ID NO 23
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
```

```
<221> NAME/KEY: modified_base
<222> LOCATION: (1)..(1)
<223> OTHER INFORMATION: "h" indicates compound 27 (2-thio-2'-
      deoxythymidine)

<400> SEQUENCE: 23 htttttttttt ttaggtcaat act                                              23

<210> SEQ ID NO 24
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(1)
<223> OTHER INFORMATION: "h" indicates compound 27 (2-thio-2'-
      deoxythymidine)

<400> SEQUENCE: 24 htttttttttt tagtattgac cta                                              23

<210> SEQ ID NO 25
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(1)
<223> OTHER INFORMATION: "h" indicates compound 28 (6-thio-2'-
      deoxyguanosine)

<400> SEQUENCE: 25 htttttttttt ttaggtcaat act                                              23

<210> SEQ ID NO 26
<211> LENGTH: 23
<212> TYPE: DNA
<213> ORGANISM: Artificial Sequence
<220> FEATURE:
<223> OTHER INFORMATION: Oligonucleotide Sequence
<220> FEATURE:
<221> NAME/KEY: modified_base
<222> LOCATION: (1)..(1)
<223> OTHER INFORMATION: "h" indicates compound 28 (6-thio-2'-
      deoxyguanosine)

<400> SEQUENCE: 26 htttttttttt tagtattgac cta                                              23

<210> SEQ ID NO 27
<211> LENGTH: 10
<212> TYPE: DNA
<213> ORGANISM: Artificial Sequence
<220> FEATURE:
<223> OTHER INFORMATION: Oligonucleotide Sequence

<400> SEQUENCE: 27
tttttttttt                                                              10
```